(12) United States Patent
Yu et al.

(10) Patent No.: US 11,479,527 B2
(45) Date of Patent: *Oct. 25, 2022

(54) HIGH PENETRATION PRODRUG COMPOSITIONS OF MUSTARDS AND MUSTARD-RELATED COMPOUNDS

(71) Applicant: Techfields Pharma Co., Ltd., Jiangsu (CN)

(72) Inventors: Chongxi Yu, Plainfield, IL (US); Lina Xu, Shanghai (CN)

(73) Assignee: Techfields Pharma Co., Ltd., Suzhou (CN)

( * ) Notice: Subject to any disclaimer, the term of this patent is extended or adjusted under 35 U.S.C. 154(b) by 0 days.

This patent is subject to a terminal disclaimer.

(21) Appl. No.: 16/209,744

(22) Filed: Dec. 4, 2018

(65) Prior Publication Data

US 2019/0233367 A1    Aug. 1, 2019

Related U.S. Application Data

(63) Continuation of application No. 12/418,564, filed on Apr. 3, 2009, now Pat. No. 10,189,774, which is a continuation-in-part of application No. PCT/IB2006/053619, filed on Oct. 3, 2006.

(51) Int. Cl.
| | | |
|---|---|---|
| *C07C 233/47* | (2006.01) | |
| *C07C 229/42* | (2006.01) | |
| *C07F 9/24* | (2006.01) | |

(52) U.S. Cl.
CPC .......... *C07C 233/47* (2013.01); *C07C 229/42* (2013.01); *C07F 9/242* (2013.01); *C07F 9/2429* (2013.01); *C07F 9/2458* (2013.01)

(58) Field of Classification Search
CPC ..... C07C 233/47; C07C 229/42; C07F 9/242; C07F 9/2429; C07F 9/2458
USPC ........................................................ 514/124
See application file for complete search history.

(56) References Cited

U.S. PATENT DOCUMENTS

| | | |
|---|---|---|
| 5,091,552 A | 2/1992 | Farquhar |
| 5,659,061 A | 8/1997 | Glazier |
| 5,691,371 A | 11/1997 | Denny et al. |
| 5,773,435 A | 6/1998 | Kadow et al. |
| 6,005,002 A | 12/1999 | Springer et al. |
| 6,137,003 A | 10/2000 | Ono et al. |
| 6,638,528 B1 | 10/2003 | Kanios |
| 6,759,406 B1 | 7/2004 | Madelmont et al. |
| 6,852,755 B1 | 2/2005 | Springer et al. |
| 6,916,949 B2 | 7/2005 | Springer et al. |
| 2002/0019343 A1 | 2/2002 | Kratz |

FOREIGN PATENT DOCUMENTS

| | | |
|---|---|---|
| CN | 1370161 A | 9/2002 |
| EP | 0364417 A1 | 4/1990 |
| WO | 1996/020011 A1 | 7/1996 |
| WO | 2001/000621 A1 | 1/2001 |

OTHER PUBLICATIONS

Sunel et al. in Revue Roumaine de Chimie (1995), 40(7-8), 773-778 (Year: 1995).*
Shaner et al. in Pesticide Biotransformation in Plants and Microorganisms (Hall, J. et al.); ACS Symposium Series, American Chemical Society: Washington, DC, 2000 (Year: 2001).*
Faissat. L., et al., "New Nitrogen Mustards Structurally Related to (L)-Carnitine"; Bio. Med. Chem. (2003); vol. 11; pp. 325-334.
DMEM at www.fishersci.com/shop/products/hyclone-dmem-f12-1-1-media-12/p-7058055 (retrieved from the Internet Apr. 30, 2018); (Year: 2018).
Bastin, R. J. et al., "Salt Selection and Optimisation Procedures for Pharmaceutical New Chemical Entities"; Organic Process Research & Development (2000); vol. 4; 427-435.
Nguyen, H. N. "Brief Synthetic Method of [N-bis (2-acyloxyethyl) Amino Acetic Acid"; vol. 45:7, pp. 7-10.
Agadzhanyan, et al., "Amino Acids and Peptides"; in Armyanskii Khimicheskii Zhurnal (1974); vol. 27:11; pp. 997-999.
Ito, N. et al., "A Medium-Term Rat Liver Bioassay for Rapid in vivo Detection of Carcinogenic Potential of Chemicals" Cancer Sci (2003); vol. 94; pp. 3-8.
Carmichael, J. et al., "Glutathione and Glutathione Transferase Levels in Mouse Granulocytes Following Cyclophosphamide Administration"; Cancer Research (1986); vol. 46; pp. 735-739.
Montgomery, J. A. et al., "Synthesis and Structure-Activity Relationships of Pre-Activated Analogs of Cyclophosphamide (NSC-26271)"; Cancer Treatments Reports (1976); vol. 60:4; 381-93.
Extended European Search Report for EP Application No. 06 809 490.3, dated Oct. 18, 2011 (6 pages).
Extended European Search Report for EP Application No. 14 15 6554.9, dated Sep. 23, 2014 (7 pages).
Burger's Medial Chemistry and Drug Discovery; Fifth Ed. vol. 1: Principles and Practice (1995); editor Wolff, John Wiley & Sons, Inc. New York, pp. 975-977.

(Continued)

Primary Examiner — Yevgeny Valenrod
(74) Attorney, Agent, or Firm — Fox Rothschild LLP

(57) ABSTRACT

The invention provides compositions of novel high penetration compositions (HPC) or high penetration prodrugs (HPP) of mustards and mustard-related compounds, which are capable of crossing biological barriers with high penetration efficiency. The HPPs are capable of being converted to parent active drugs or drug metabolites after crossing the biological barrier and thus can render treatments for the conditions that the parent drugs or metabolites can. Additionally, the HPPs are capable of reaching areas that parent drugs may not be able to access or to render a sufficient concentration at the target areas and therefore render novel treatments. The HPPs can be administered to a subject through various administration routes, e.g., locally delivered to an action site of a condition with a high concentration or systematically administered to a biological subject and enter the general circulation with a faster rate.

10 Claims, 1 Drawing Sheet

(56) References Cited

OTHER PUBLICATIONS

Testa, B. "Prodrug Research: Futile or Fertile"; Bio. Pharma. (2004); vol. 68; pp. 2097-2106.
Modern Pharmaceutics, 3rd Edition (1996); editor Banker, Marcel Dekker, Inc. New York, 2 pgs.
Paudel, K. S. et al., "Challenges and Opportunities in Dermal/ Transdermal Delivery"; Ther. Deliv. (2010); vol. 1:1; pp. 109-131.
Cannon, J. G., Chapter Nineteen in Burger's Medicinal Chemistry and Drug Discovery, Fifth Edition, vol. I: Principles and Practice, Wiley-I nterscience (1995); pp. 783-802, 784.
Berge, S. M., et al., "Pharmaceuticals Salts"; J. Pharma Sci. (1977) vol. 66:1; pp. 1-19.
Milosovich, S., et al., "Testosteronyl-4-Dimethylaminobutyrate-HCI: A Prodrug with Improved Skin Penetration Rate," J. Pharm. Sci. (1993), vol. 82(2); pp. 227-228.

Korean Intellectual Property Office, Written Opinion of the International Searching Authority for PCT/IB2006/053619, dated Jun. 26, 2007.
Wolf, M. et al., "Alkylating Benzamides with Melanoma Cytotoxicity"; Melanoma Research (2004); vol. 14; pp. 353-360.
Shaner, D L. et al., Chapter 19 in Pesticide Biotransformation in Plants and Microorganisms (Hall, J. et al.); ACS Symposium Series, American Chemical Society (2000); Washington, DC.
Sunel, V. et al., "Kinetic Studies and Analytical Determinations on Some Derivatives of L-Asparagic Acid Acting as Antimetabolites and Alkylating Agents"; in Revue Roumaine de Chimie (1995); vol. 40:7-8; pp. 773-778.
Klyukene, R. B. et al., "Synthesis of N-p-[di(2-chloroethyl)amino]phenacetylvalylmethionine diastereomers"; in Russ Chem Bull (1976); vol. 25; pp. 1950-1953.

* cited by examiner

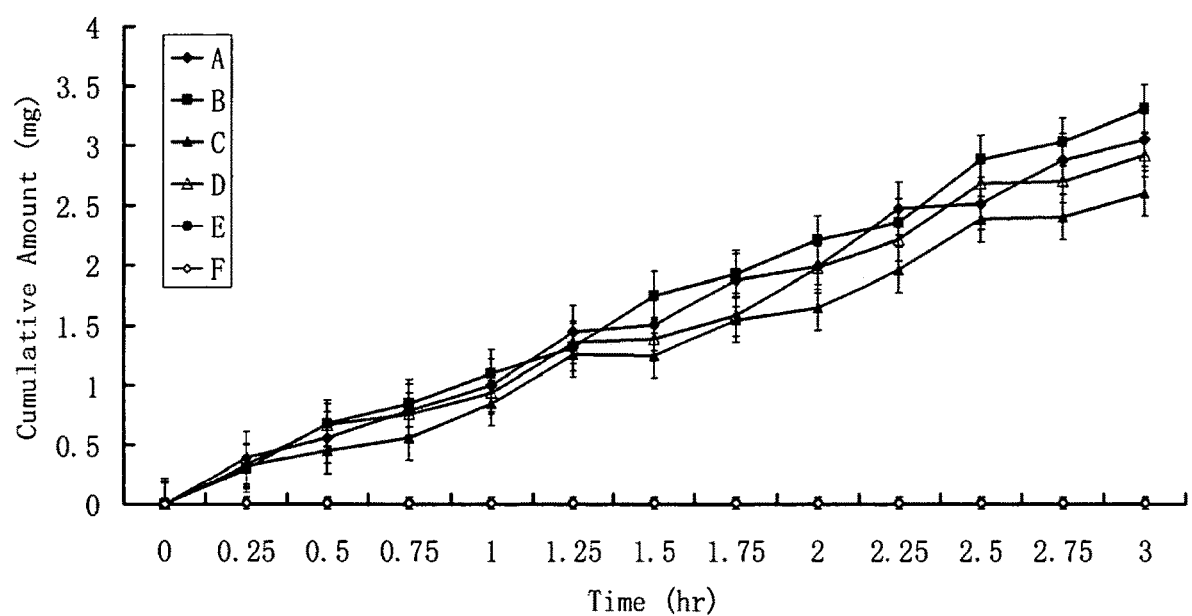

HIGH PENETRATION PRODRUG COMPOSITIONS OF MUSTARDS AND MUSTARD-RELATED COMPOUNDS

CROSS-REFERENCE TO RELATED APPLICATIONS

The present application is a continuation-in-part application of International Application PCT/IB2006/053619, filed Oct. 3, 2006 and published Apr. 10, 2008 with International Publication Number WO2008/041059, which is incorporated herein by reference in its entirety.

FIELD OF THE INVENTION

This invention relates to the field of pharmaceutical compositions capable of penetrating one or more biological barriers and methods of using the pharmaceutical compositions for preventing, diagnosing and/or treating condition or disease in human and animals that are treatable by mustards or mustard-related compounds. The invention also relates to methods of using the pharmaceutical compositions for screening new drug candidates and methods of using the pharmaceutical compositions for diagnosing a condition in a biological subject.

BACKGROUND OF THE INVENTION

Mustards are alkylating agents and are very reactive. For example, mustards can react with DNA, RNA, and enzymes and have been used to kill cancer cells in chemotherapy.

Mustards and mustard-related compounds have been used for treatment of leukemias, breast, ovarian, and lung cancer. For example, Springer, et al. designed and synthesized many nitrogen mustard compounds for the treatment of cancers (Springer, C. J. ea al. U.S. Pat. Nos. 6,852,755, 6,916,949, and 6,005,002). Denny, et al. discussed the synthesis of nitrobenzyl mustard quaternary salts and their use as hypoxia-selective cytotoxic agents (Denny, W. A. et al, U.S. Pat. No. 5,691,371). Glazier described prodrugs of phosphoramide mustard, isophosphoramide mustard and analogs (Glazier, A. U.S. Pat. No. 5,659,061). Farquhar designed and synthesized novel antitumor aldophosphamide analogs (Glazier, A. U.S. Pat. No. 5,091,552). Mustards and mustard-related compounds are also used to treat psoriasis.

However, mustards and mustard-related compounds also cause adverse side effects. Common side effects of present chemotherapy using mustards or mustard-related compounds include, for example, nausea, vomiting, diarrhea, loss of appetite, hair loss, and increased susceptibility to infection. Such side effects are often dose-dependent.

Modifications of mustards have been reported to improve their efficacy and decrease their side effects. For example, Kadow et al. described the delivery of antitumor drugs to tumor cells by the administration of a tumor-selective antibody-beta-lactamase conjugate that binds to tumor cells (Kadow, J. et al. U.S. Pat. No. 5,773,435). However, these agents are administered orally or systematically. Oral or systematical administrations require a much higher plasma concentration of the active agents to produce a therapeutically effective local concentration at the particular site of condition or disease, e.g., cancer or infection.

Therefore, a need exists in the art for novel compositions that are capable of being delivered efficiently and effectively to the action site of a condition (e.g., a disease) to prevent, reduce or treat conditions as well as minimize adverse side effects.

SUMMARY OF THE INVENTION

One aspect of the invention is directed to a high penetration prodrug (HPP) or high penetration composition (HPC) comprising a functional unit covalently linked to a transportational unit through a linker. The terms "HPP" and "HPC" are used alone or together herein and are interchangeable unless specifically noted.

In certain embodiments, a functional unit of a HPP or HPC comprises a moiety of an agent, wherein the efficient and effective delivery of the agent to a biological subject and/or transportation of the agent across one or more biological barriers are/is desired.

In certain embodiments, a functional unit may be hydrophilic, lipophilic, or amphiphilic (i.e., both hydrophilic and lipophilic). For example, the lipophilic nature of a function unit may be inherent or achieved by converting the hydrophilic moieties of a functional unit to lipophilic moieties.

In certain embodiments, a functional unit of a HPP or HPC comprises a moiety of a mustard or mustard-related compound. A mustard-related compound is an analog of a mustard or mustard metabolite, a mustard metabolite; or an agent that can be metabolized into a mustard or mustard metabolite after the HPP or HPC penetrates one or more biological barriers. Examples of mustards include, but are not limited to, nitrogen mustards, nitrobenzyl mustards, phosphoramide mustard, isophosphoramide mustards and aldophosphamide.

In certain embodiments, a transportational unit of a HPP or HPC comprises a protonatable amine group that is capable of facilitating or enhancing the transportation or crossing of the HPP or HPC through one or more biological barriers. In certain embodiments, the protonatable amine group is substantially protonated at the pH of the biological barriers through which a HPP or HPC penetrates. In certain embodiments, the amine group can be reversibly protonated or deprotonated.

In certain embodiments, a linker covalently links the functional unit to the transportational unit of a HPP and comprises a bond that is capable of being cleaved after the HPP penetrates across one or more biological barriers. The cleavable bond comprises, for example, a covalent bond, an ether, a thioether, an amide, an ester, a thioester, a carbonate, a carbamate, a phosphate or an oxime bond.

Another aspect of the invention relates to a pharmaceutical composition comprising at least one HPP or HPC of a mustard or mustard-related compound and a pharmaceutically acceptable carrier.

Another aspect of the invention relates to a method for penetrating a biological barrier using a HPP or HPC of a mustard or mustard-related compound.

Another aspect of the invention relates to a method for diagnosing the onset, development, or remission of a condition in a biological subject by using a HPP or HPC of a mustard or mustard-related compound. In certain embodiments, the HPP (or HPC) or the functional unit thereof is detectable. In certain embodiments, the HPP or the functional unit of the HPP is inherently detectable, labeled with, or conjugated to, a detectable marker.

Another aspect of the invention relates to a method for screening functional units, linkers, or transportational units for desired characteristics.

Another aspect of the invention relates to a method for preventing, ameliorating, or treating a condition in a biological subject by administering to the subject a composition in accordance with the invention. In certain embodiments, the method relates to treating a condition in a subject treatable by mustards or mustard-related compounds by administering to the subject a therapeutically effective amount of a HPP of a mustard or mustard-related compound, or a pharmaceutical composition thereof. In certain embodiments, the pharmaceutical composition of the HPP is administrated to a biological subject via various routes including, but not limited to, oral, enteral, buccal, nasal, topical, rectal, vaginal, aerosol, transmucosal, epidermal, transdermal, dermal, ophthalmic, pulmonary, subcutaneous, and/or parenteral routes. In certain preferred embodiments, the pharmaceutical composition of HPP is administered orally, transdermally, topically, subcutaneously and/or parenterally.

In accordance with the advantages of the invention, without intending to be limited by any particular mechanism, a therapeutically effective amount of a HPP or HPC can be administered locally to a site of condition with a less dosage at a higher concentration. The advantages of the invention also include, for example, avoidance of systematic administration, reduction of adverse effects (e.g., pain of injection, gastrointestinal/renal effects, and other side effect), and possible novel treatments due to high local concentration of a HPP, HPC or active agent. The advantages further include, for example, systematic administration of a HPP or HPC to a biological subject to achieve faster and more efficient bioavailability, penetration of biological barriers (e.g., the blood brain barrier) which have been difficult to cross, and new indications as a result of passing through biological barriers.

BRIEF DESCRIPTION OF THE FIGURES

FIG. 1: Cumulative amounts of N,N-diethylaminoethyl 4-[bis(2-chloroethyl)amino]benzenebutyrate.HBr (A, 20% solution), 4-[bis(2-chloroethyl)amino]-N-acetyl-L-phenylalanine N,N-diethylaminoethyl ester hydrobromide (B, 20% solution), N,N-bis(2-chloroethyl)aminophosphamide N,N-diethylaminoethyl ester hydrobromide (C, 10% solution), diethylaminoethyl 4-[bis(2-methylsulfonylethyl)amino]benzenebutyrate.HCl (D, 10% solution), chlorambucil (E, 20% suspension), and melphalan (F, 20% suspension) crossing isolated human skin tissue in Franz cells (n=5). In each case, the vehicle was pH 7.4 phosphate buffer (0.2 M).

DETAILED DESCRIPTION OF THE INVENTION

I. Structures of High Penetration Prodrug (HPP) or High Penetration Composition (HPC)

One aspect of the invention is directed to a high penetration prodrug (HPP) or a high penetration composition (HPC). The term "high penetration prodrug" or "HPP" or "high penetration composition" or "HPC" as used herein refers to a composition comprising a functional unit covalently linked to a transportational unit through a linker.

A functional unit of a HPP or HPC which comprises a moiety of a parent drug has the properties of: 1) the delivery of the parent drug or the HPP into a biological subject and/or the transportation of the parent drug across a biological barrier are/is desired, 2) the HPP is capable of penetrating or crossing a biological barrier, and 3) the HPP is capable of being cleaved so as to turn the moiety of a parent drug into the parent drug or a metabolite of the parent drug.

In certain embodiments, a functional unit may be hydrophilic, lipophilic, or amphiphilic (hydrophilic and lipophilic). The lipophilic moiety of the function unit may be inherent or achieved by converting its hydrophilic moieties to lipophilic moieties. For example, a lipophilic moiety of a functional unit is produced by converting one or more hydrophilic groups of the functional unit to lipophilic groups via traditional organic synthesis. Examples of the hydrophilic groups include, without limitation, carboxylic, hydroxyl, thiol, amine, phosphate/phosphonate and carbonyl groups. The lipophilic moieties produced via the modification of these hydrophilic groups include, without limitation, ethers, thioethers, esters, thioesters, carbonates, carbamates, amides, phosphates and oximes.

In certain embodiments, a parent drug of a HPP or HPC is selected from the group consisting of a mustard and mustard-related compound. The moiety of a mustard or mustard-related compound can be further converted to a lipophilic moiety as described supra.

Mustards are well known in the art and are used in connection with various conditions. Examples of mustards and mustard-related compounds include, but are not limited to, nitrogen mustards, nitrobenzyl mustards, phosphoramide mustard, isophosphoramide mustards and aldophosphamide.

In one embodiment, a functional unit of a HPP of a mustard and mustard-related compound comprises a moiety having a structure selected from the group consisting of Structure A and Structure B:

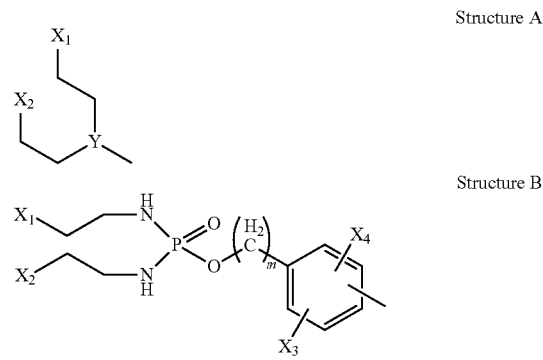

including stereoisomers and pharmaceutically acceptable salts thereof, wherein:

is selected from the group consisting of Structure Y-a, Structure Y-b, Structure Y-c, Structure Y-d, and Structure Y-e:

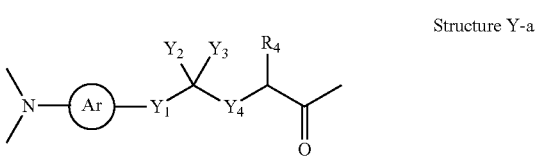

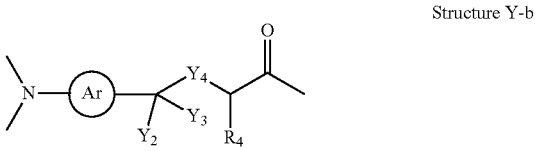

-continued

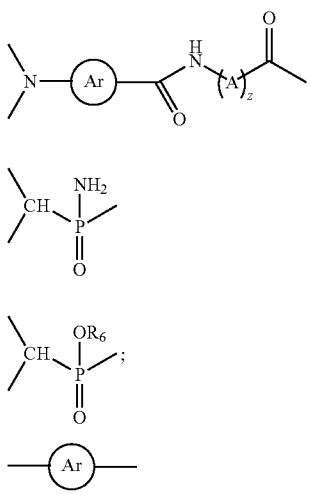

is selected from the group consisting of substituted and unsubstituted aryl, Structure Ar-a, Structure Ar-b, Structure Ar-c, Structure Ar-d, Structure Ar-e, Structure Ar-f, Structure Ar-g, Structure Ar-h and Structure Ar-i:

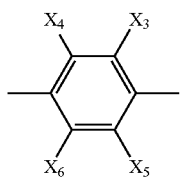
Structure Ar-a

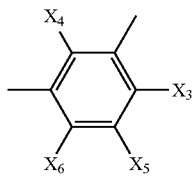
Structure Ar-b

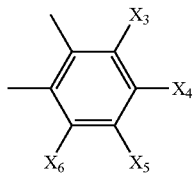
Structure Ar-c

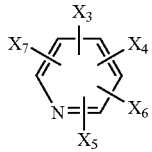
Structure Ar-d

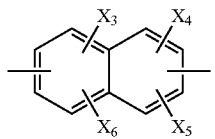
Structure Ar-e

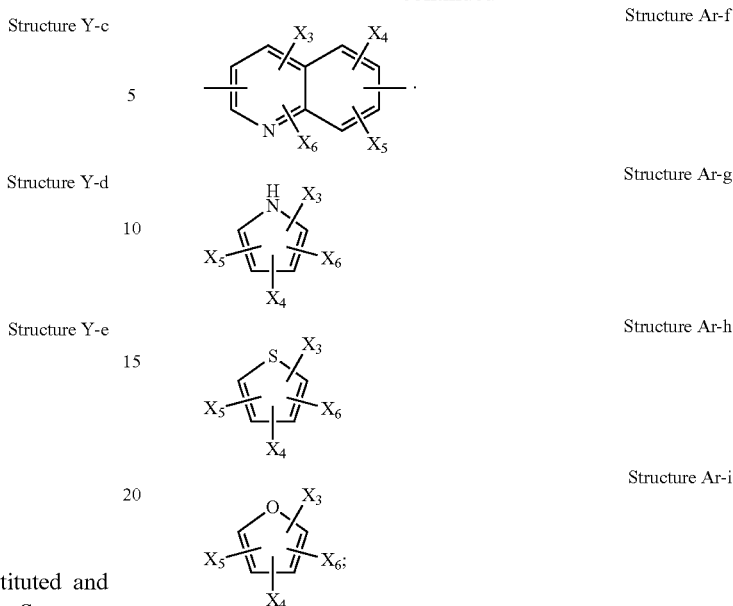

$X_1$ and $X_2$ are independently selected from the group consisting of Cl, Br, F, I, and $OSO_2R_4$;

$R_4$ and $R_6$ are independently selected from the group consisting of substituted and unsubstituted alkyl, substituted and unsubstituted alkoxyl, substituted and unsubstituted perfluoroalkyl, substituted and unsubstituted alkyl halide, substituted and unsubstituted aryl, and substituted and unsubstituted heteroaryl groups;

$X_3$-$X_7$ are independently selected from the group consisting of $NHCOR_4$, $OR_4$, $SR_4$, $NHR_4$, $OCOR_4$, $R_4$, substituted and unsubstituted alkoxyl, substituted and unsubstituted alkylthio, substituted and unsubstituted alkylamino, substituted and unsubstituted alkyl halide, H, F, Cl, Br, I, $NO_2$, CN, $CF_3$, $NHCOCH_3$, $OCH_3$, $SCH_3$, $NH_2$, $NHCH_3$, $OCOCH_3$, $OCOC_2H_5$, $OC_2H_5$, $OC_3H_7$, $CH_3$, $C_2H_5$, and $C_3H_7$;

m, n and z are the same or different integers;

$Y_1$ is selected from the group consisting of $CH_2$, O, S, and NH;

$Y_2$ and $Y_3$ are the same or different and each is $NHCOR_4$, H, OH, $NHCOCH_3$, $NHCOC_2H_5$, Cl, F, Br, or I, or taken together is =O;

$Y_4$ is selected from the group consisting of $R_4$, $CH_2$, —$(CH_2)_n$—, O, S, and NH;

A is selected from the group consisting of α-amino acids, β-amino acids, and amino acids residues;

any $CH_2$ groups may be replaced with O, S, or NH; and when a bond is not linked with any atom of an aryl or heteroaryl ring, the bond can be put into any position of the ring.

In certain embodiments, the functional unit of a HPP of a mustard and mustard-related compound comprises a moiety having a structure selected from the group consisting of Structure A and Structure B as defined supra, including stereoisomers and pharmaceutically acceptable salts thereof, wherein $R_4$ is selected from the group consisting of H, substituted and unsubstituted 1 to 20 carbon atoms alkyl, substituted and unsubstituted 1 to 20 carbon atoms alkoxyl, substituted and unsubstituted 1 to 20 carbon atoms alkenyl, substituted and unsubstituted 1 to 20 carbon atoms perfluoroalkyl, substituted and unsubstituted 1 to 20 carbon atoms alkyl halide, substituted and unsubstituted 1 to 20 carbon atoms alkynyl, substituted and unsubstituted 1 to 20 carbon atoms aryl, and substituted and unsubstituted 1 to 20 carbon atoms heteroaryl moieties.

In certain embodiments, the functional unit of a HPP of a mustard and mustard-related compound comprises a moiety having a structure of Structure B as defined supra, including stereoisomers and pharmaceutically acceptable salts thereof, wherein m is selected from the group consisting of 0, 1, 2, 3, 4, 5, 6, 7, 8, 9, 10, 11, 12 . . . and 100.

In certain embodiments, the functional unit of a HPP of a mustard and mustard-related compound comprises a moiety having a structure of Structure A as defined supra, including stereoisomers and pharmaceutically acceptable salts thereof, wherein n is selected from the group consisting of 0, 1, 2, 3, 4, 5, 6, 7, 8, 9, 10, 11, 12, 13, 14, 15, 16, 17, 18, 19, 20 . . . , and 100.

As used herein, the term "pharmaceutically acceptable salt" means those salts of compounds of the invention that are safe for application in a subject. Pharmaceutically acceptable salts include salts of acidic or basic groups present in compounds of the invention. Pharmaceutically acceptable acid addition salts include, but are not limited to, hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, p-toluenesulfonate and pamoate (i.e., 1,11-methylene-bis-(2-hydroxy-3-naphthoate)) salts. Certain compounds of the invention can form pharmaceutically acceptable salts with various amino acids. Suitable base salts include, but are not limited to, aluminum, calcium, lithium, magnesium, potassium, sodium, zinc, and diethanolamine salts. For a review on pharmaceutically acceptable salts see BERGE ET AL., 66 J. PHARM. SCI. 1-19 (1977), incorporated herein by reference.

As used herein, unless specified otherwise, the term "alkyl" means a branched or unbranched, saturated or unsaturated, monovalent or multivalent hydrocarbon group. Examples of alkyl include, but are not limited to, methyl, ethyl, propyl, isopropyl, butyl, isobutyl, t-butyl, pentyl, hexyl, heptyl, octyl, nonyl, decyl, undecyl, dodecyl, ethenyl, propenyl, butenyl, isobutenyl, pentenyl, hexenyl, heptenyl, octenyl, nonenyl, decenyl, undecenyl, dodecenyl, ethynyl, propynyl, butynyl, isobutynyl, pentynyl, hexynyl, heptynyl, octynyl, nonynyl, decynyl, undecynyl, dodecynyl, methylene, ethylene, propylene, isopropylene, butylene, isobutylene, t-butylene, pentylene, hexylene, heptylene, octylene, nonylene, decylene, undecylene and dodecylene, In certain embodiments, the hydrocarbon group contains 1 to 30 carbons. In certain embodiments, the hydrocarbon group contains 1 to 20 carbons As used herein, unless specified otherwise, the term "cycloalkyl" means an alkyl which contains at least one ring and no aromatic rings. Examples of cycloalkyl include, but are not limited to, cyclopropyl, cyclobutyl, cyclopentyl, cyclohexyl, cycloheptyl, cyclooctyl, cyclononyl, cyclodecyl, cycloundecyl and cyclododecyl. In certain embodiments, the hydrocarbon chain contains 1 to 30 carbons. In certain embodiments, the hydrocarbon group contains 1 to 20 carbons.

As used herein, unless specified otherwise, the term "heterocycloalkyl" means a cycloalkyl wherein at least one ring atom is a non-carbon atom. Examples of the non-carbon ring atom include, but are not limited to, S, O and N.

As used herein, unless specified otherwise, the term "alkoxyl" means an alkyl, cycloalkyl or heterocycloalkyl, which contains one or more oxygen atoms. Examples of alkoxyl include, but are not limited to, —CH$_2$—OH, —OCH$_3$, —O-alkyl, -alkyl-OH, -alkyl-O-alkyl-, wherein the two alkyls can be the same or different.

As used herein, unless specified otherwise, the term "alkyl halide" means an alkyl, cycloalkyl or heterocycloalkyl, which contains one or more halogen atoms, wherein the halogen atoms can be the same or different. The term "halogen" means fluorine, chlorine, bromine or iodine. Examples of alkyl halide include, but are not limited to, -alkyl-F, -alkyl-Cl, -alkyl-Br, -alkyl-I, -alkyl(F)—, -alkyl (Cl)—, -alkyl(Br)— and -alkyl(I)—.

As used herein, unless specified otherwise, the term "alkylthio" means an alkyl, cycloalkyl or heterocycloalkyl, which contains one or more sulfur atoms. Examples of alkylthio include, but are not limited to, —CH$_2$—SH, —SCH$_3$, —S-alkyl, -alkyl-SH, -alkyl-S-alkyl-, wherein the two alkyls can be the same or different.

As used herein, unless specified otherwise, the term "alkylamino" means an alkyl, cycloalkyl or heterocycloalkyl, which contains one or more nitrogen atoms. Examples of alkylamino include, but are not limited to, —CH$_2$—NH, —NCH$_3$, —N(alkyl)-alkyl, —N-alkyl, -alkyl-NH$_2$, -alkyl-N-alkyl and -alkyl-N(alkyl)-alkyl wherein the alkyls can be the same or different.

As used herein, unless specified otherwise, the term "perfluoroalkyl" means an alkyl, cycloalkyl or heterocycloalkyl, which contains one or more fluoro group, including, without limitation, perfluoromethyl, perfluoroethyl, perfluoropropyl.

As used herein, unless specified otherwise, the term "aryl" means a chemical structure comprising one or more aromatic rings. In certain embodiments, the ring atoms are all carbon. In certain embodiments, one or more ring atoms are non-carbon, e.g. oxygen, nitrogen, or sulfur. Examples of aryl include, without limitation, phenyl, benzyl, naphthalenyl, anthracenyl, pyridyl, quinoyl, isoquinoyl, pyrazinyl, quinoxalinyl, acridinyl, pyrimidinyl, quinazolinyl, pyridazinyl, cinnolinyl, imidazolyl, benzimidazolyl, purinyl, indolyl, furanyl, benzofuranyl, isobenzofuranyl, pyrrolyl, indolyl, isoindolyl, thiophenyl, benzothiophenyl, pyrazolyl, indazolyl, oxazolyl, benzoxazolyl, isoxazolyl, benzisoxazolyl, thiaxolyl and benzothiazolyl.

In certain embodiments, a transportational unit of a HPP comprises a protonatable amine group that is capable of facilitating the transportation or crossing of the HPP through one or more biological barriers (e.g., >about 50 times, >about 100 times, >about 300 times, >about 500 times, >about 1,000 times faster than the parent drug). In certain embodiments, the protonatable amine group is substantially protonated at a physiological pH. In certain embodiments, the amine group can be reversibly protonated. In certain embodiments, the transportational unit may or may not be cleaved from the functional unit after the penetration of HPP through one or more biological barriers.

In certain embodiments, the protonatable amine group is selected from the group consisting of pharmaceutically acceptable substituted and unsubstituted primary amine groups, pharmaceutically acceptable substituted and unsubstituted secondary amine groups, and pharmaceutically acceptable substituted and unsubstituted tertiary amine groups.

In certain embodiments, the protonatable amine group is selected from the group consisting of Structure Na, Structure Nb, Structure Nc, Structure Nd, Structure Ne, Structure Nf, Structure Ng, Structure Nh, Structure Ni, Structure Nj, Structure Nk, Structure Nl, Structure Nm, Structure Nn, Structure No, Structure Np, Structure Nq and Structure Nr:

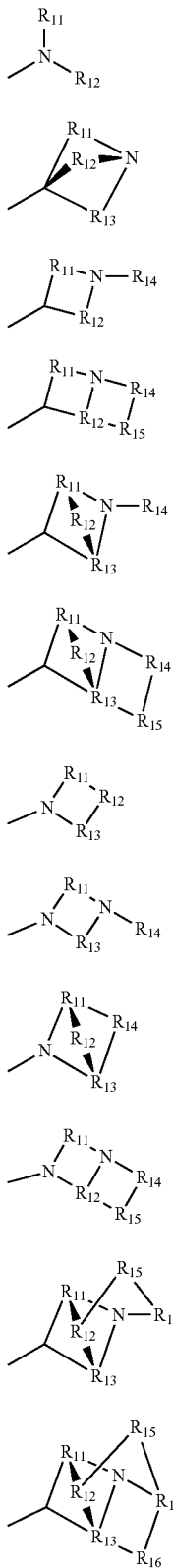

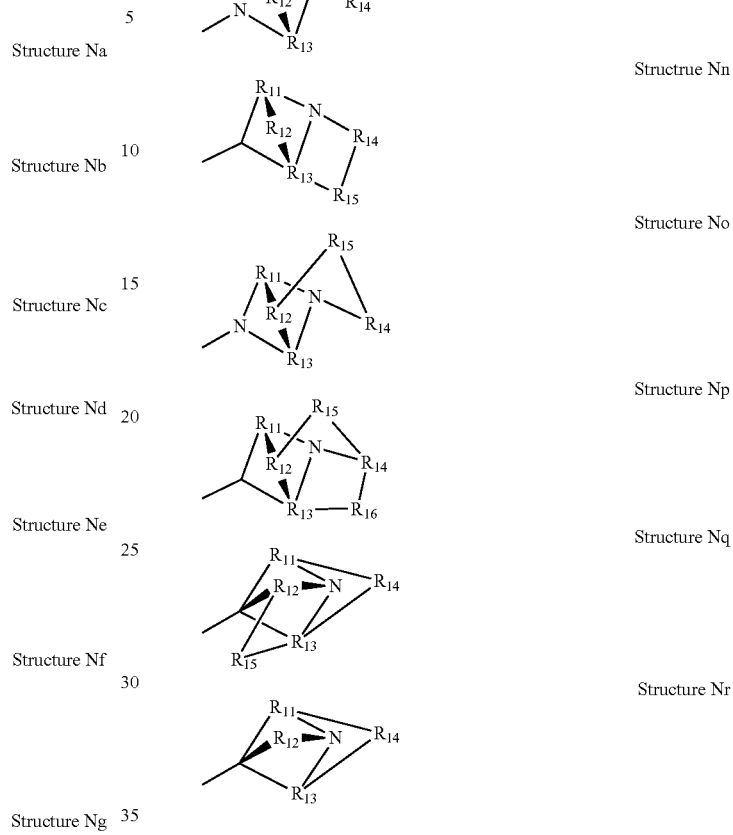

including stereoisomers and pharmaceutically acceptable salts thereof.

As used herein, unless specified otherwise, each $R_{11}$-$R_{16}$ is independently selected from the group consisting of nothing, H, $CH_2COOR_{11}$, substituted and unsubstituted alkyl, substituted and unsubstituted cycloalkyl, substituted and unsubstituted heterocycloalkyl, substituted and unsubstituted aryl, substituted and unsubstituted heteroaryl, substituted and unsubstituted alkoxyl, substituted and unsubstituted alkylthio, substituted and unsubstituted alkylamino, substituted and unsubstituted perfluoroalkyl, and substituted and unsubstituted alkyl halide, wherein any carbon or hydrogen may be further independently replaced with O, S, P, $NR_{11}$, or any other pharmaceutically acceptable groups.

In certain embodiments, a linker covalently linking a functional unit and a transportational unit of a HPP comprises a bond that is capable of being cleaved after the HPP penetrates across one or more BBs. The cleavable bond comprises, for example, a covalent bond, an ether, thioether, amide, ester, thioester, carbonate, carbamate, phosphate or oxime bond.

In certain embodiments, a HPP of a mustard and mustard-related compound has the following Structure L:

including stereoisomers and pharmaceutically acceptable salts thereof, wherein:

F is a functional unit of a HPP of a mustard or mustard-related compound. Examples of F include Structure A and Structure B as defined supra;

T is a transportational unit of a HPP of a mustard or mustard-related compound. For example, T is selected from the group consisting of Structure Na, Structure Nb, Structure Nc, Structure Nd, Structure Ne, Structure Nf, Structure Ng, Structure Nh, Structure Ni, Structure Nj, Structure Nk, Structure Nl, Structure Nm, Structure Nn, Structure No, Structure Np, Structure Nq and Structure Nr as defined supra;

$L_1$ is selected from the group consisting of nothing, O, S, —N($L_3$)-, —N($L_3$)-CH$_2$—O, —N($L_3$)-CH$_2$—N($L_5$)-, —O—CH$_2$—O—, —O—CH($L_3$)-O, and —S—CH($L_3$)-O—;

$L_2$ is selected from the group consisting of nothing, O, S, —N($L_3$)-, —N($L_3$)-CH$_2$—O, —N($L_3$)-CH$_2$—N($L_5$)-, —O—CH$_2$—O—, —O—CH($L_3$)-O, —S—CH($L_3$)-O—, —O-$L_3$-, —N-$L_3$-, —S-$L_3$-, —N($L_3$)-$L_5$- and $L_3$;

$L_4$ is selected from the group consisting of C=O, C=S,

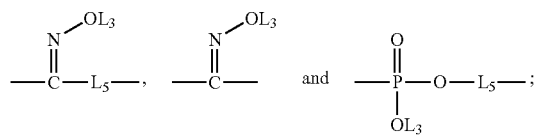

each $L_3$ and $L_5$ is independently selected from the group consisting of nothing, H, CH$_2$COOL$_6$, substituted and unsubstituted alkyl, substituted and unsubstituted cycloalkyl, substituted and unsubstituted heterocycloalkyl, substituted and unsubstituted aryl, substituted and unsubstituted heteroaryl, substituted and unsubstituted alkoxyl, substituted and unsubstituted alkylthio, substituted and unsubstituted alkylamino, substituted and unsubstituted perfluoroalkyl, and substituted and unsubstituted alkyl halide, wherein any carbon or hydrogen may be further independently replaced with O, S, P, NL$_3$, or any other pharmaceutically acceptable groups;

$L_6$ is selected from the group consisting of H, OH, Cl, F, Br, I, substituted and unsubstituted alkyl, substituted and unsubstituted cycloalkyl, and substituted and unsubstituted heterocycloalkyl, substituted and unsubstituted aryl, substituted and unsubstituted heteroaryl, substituted and unsubstituted alkoxyl, substituted and unsubstituted alkylthio, substituted and unsubstituted alkylamino, substituted and unsubstituted perfluoroalkyl, and substituted and unsubstituted alkyl halide, wherein any carbon or hydrogen may be further independently replaced with O, S, N, P(O)OL$_6$, CH=CH, C≡C, CHL$_6$, CL$_6$L$_7$, aryl, heteroaryl, or cyclic groups; and $L_7$ is selected from the group consisting of H, OH, Cl, F, Br, I, substituted and unsubstituted alkyl, substituted and unsubstituted cycloalkyl, and substituted and unsubstituted heterocycloalkyl, substituted and unsubstituted aryl, substituted and unsubstituted heteroaryl, substituted and unsubstituted alkoxyl, substituted and unsubstituted alkylthio, substituted and unsubstituted alkylamino, substituted and unsubstituted perfluoroalkyl, and substituted and unsubstituted alkyl halide, wherein any carbon or hydrogen may be further independently replaced with O, S, N, P(O)OL$_6$, CH=CH, C≡C, CHL$_6$, CL$_6$L$_7$, aryl, heteroaryl, or cyclic groups.

In certain embodiments, a HPP or HPC of a mustard or mustard-related compound comprises the structure of Structure L, including stereoisomers and pharmaceutically acceptable salts thereof, wherein F, $L_1$, $L_2$ and T are defined as supra, and $L_4$ is C=O.

Examples of HPPs of Mustards and Mustard-Related Compounds.

In certain embodiments, a HPP of a mustard and mustard-related compound includes a compound having the formula of Structure 1 or Structure 2, including stereoisomers and pharmaceutically acceptable salts thereof, wherein Structure 1 is selected from the group consisting of Structure 1a, Structure 1b, Structure 1c, Structure 1d, Structure 1e, Structure 1f, Structure 1g, Structure 1h, Structure 1i, Structure 1j, Structure 1k, Structure 1l, Structure 1m, Structure 1n, Structure 1o, Structure 1p, Structure 1q, and Structure 1r; and Structure 2 is selected from the group consisting of Structure 2a, Structure 2b, Structure 2c, Structure 2d, Structure 2e, Structure 2f, Structure 2g, Structure 2h, Structure 2i, Structure 2j, Structure 2k, Structure 2l, Structure 2m, Structure 2n, Structure 2o, Structure 2p, Structure 2q, and Structure 2r:

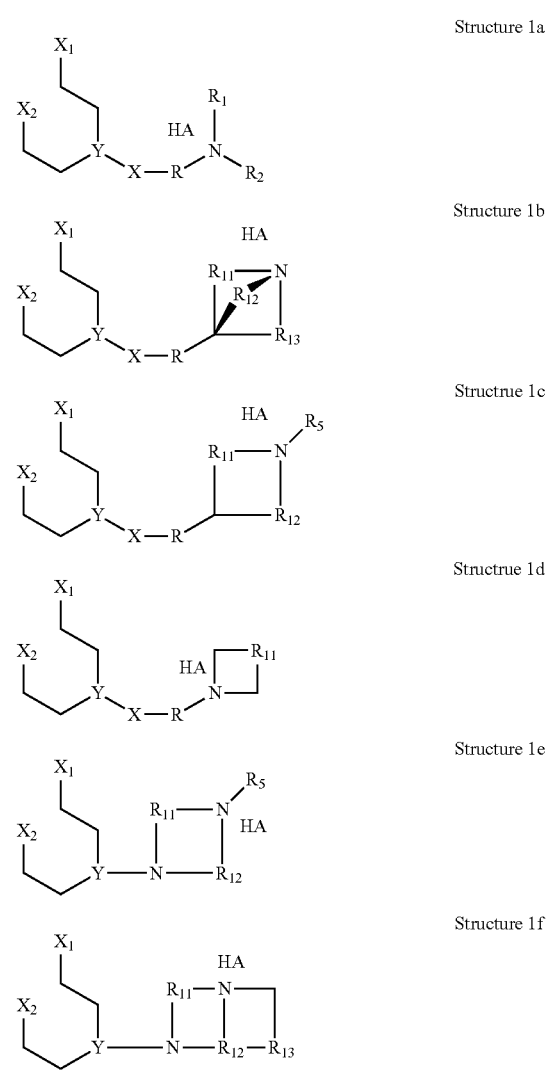

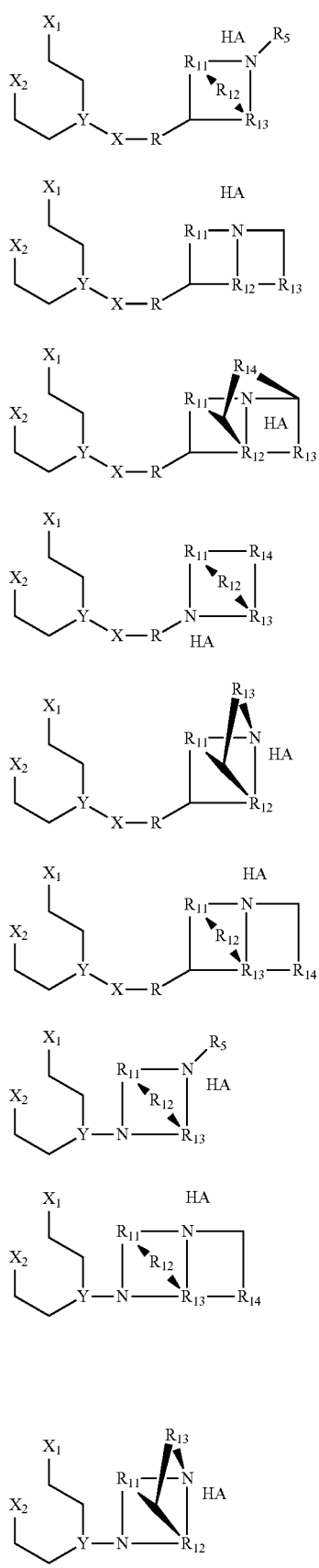
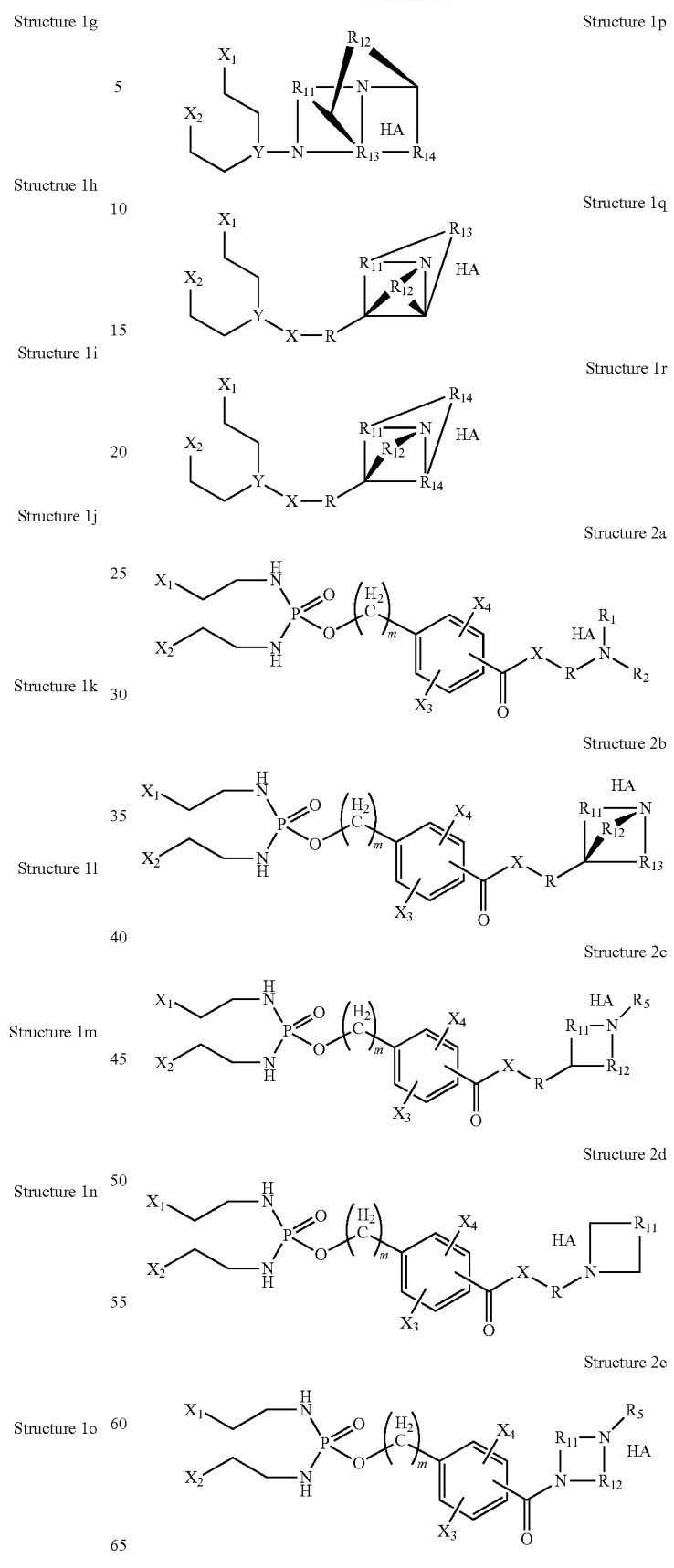

Structure 2f
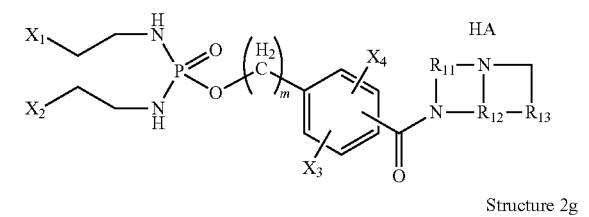

Structure 2g
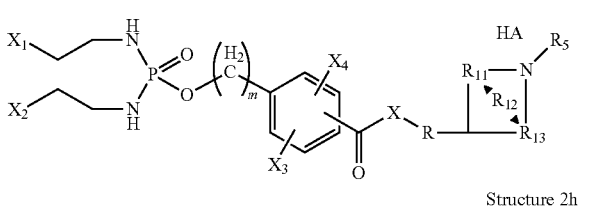

Structure 2h
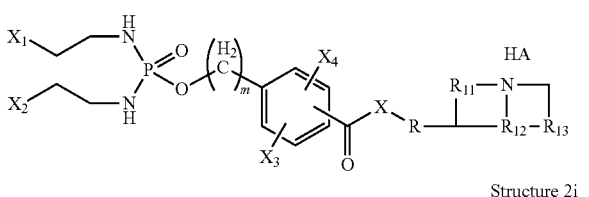

Structure 2i
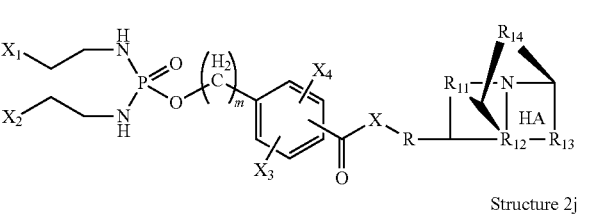

Structure 2j
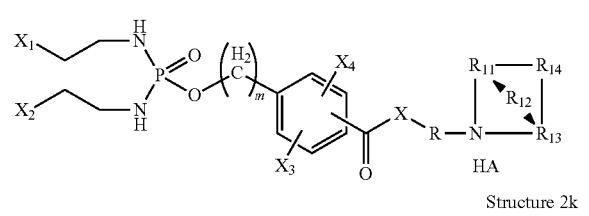

Structure 2k
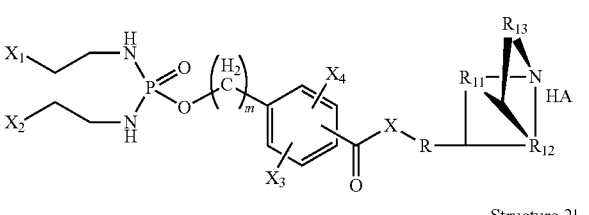

Structure 2l
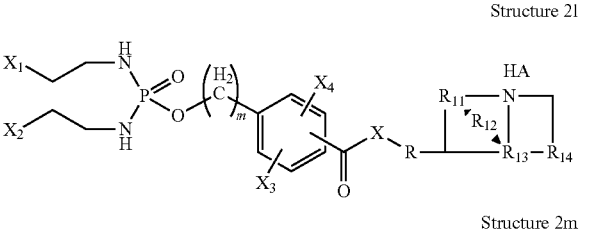

Structure 2m
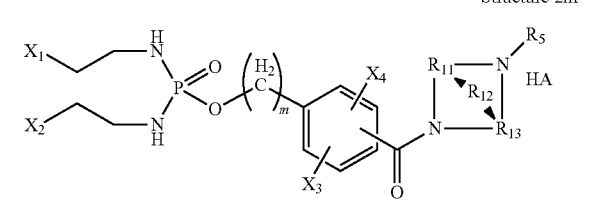

Structure 2n
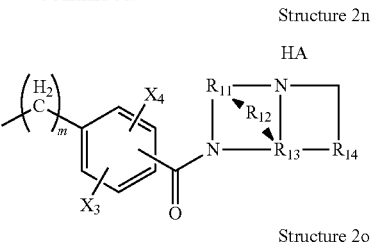

Structure 2o
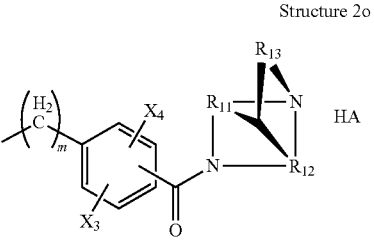

Structure 2p
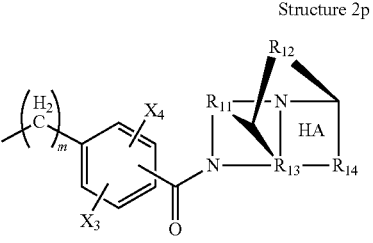

Structure 2q
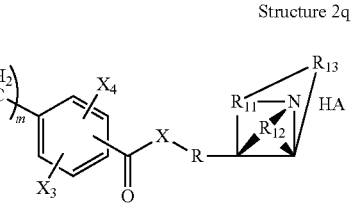

Structure 2r
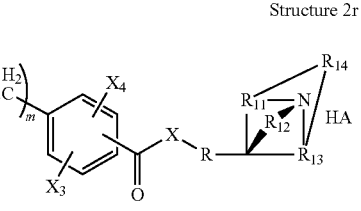

including stereoisomers and pharmaceutically acceptable salts thereof, wherein,

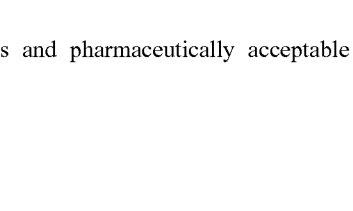

m and $X_1$-$X_4$ are defined the same as supra;

R, $R_1$, $R_2$, $R_5$ and $R_{11}$-$R_{14}$ are independently selected from the group consisting of substituted and unsubstituted 0-20 carbon atoms alkyl, substituted and unsubstituted 1-20 carbon atoms alkoxyl, substituted and unsubstituted 1-20 carbon atoms perfluoroalkyl, substituted and unsubstituted 1-20 carbon atoms alkyl halide, substituted and unsubstituted 2-20 carbon atoms alkenyl, substituted and unsubstituted 2-20 carbon atoms alkynyl, substituted and unsubstituted 6-20 carbon atoms aryl, and substituted and unsubstituted 2-20 carbon atoms heteroaryl moieties which are pharmaceutically acceptable, wherein any $CH_2$ may be replaced with O, S, $NR_5$, or other groups;

X is selected from the group consisting of O, S, $NR_5$, and NH;

any $CH_2$ groups may be replaced with O, S, or NH; and when a bond is not linked with an atom of an aryl or heteroaryl ring, the bond can be put into any position of the ring.

As used herein, the term "HA" is nothing or a pharmaceutically acceptable acid, e.g. hydrochloride, hydrobromide, hydroiodide, nitric acid, sulfic acid, bisulfic acid, phosphoric acid, phosphorous acid, phosphonic acid, isonicotinic acid, acetic acid, lactic acid, salicylic acid, citric acid, tartaric acid, pantothenic acid, bitartaric acid, ascorbic acid, succinic acid, maleic acid, gentisinic acid, fumaric acid, gluconic acid, glucaronic acid, saccharic acid, formic acid, benzoic acid, glutamic acid, methanesulfonic acid, ethanesulfonic acid, benzensulfonic acid, p-toluenesulfonic acid and pamoic acid.

II. Pharmaceutical Compositions Comprising HPPs

Another aspect of the invention relates to a pharmaceutical composition comprising at least one HPP of a mustard or mustard-related compound and a pharmaceutically acceptable carrier.

The term "pharmaceutically acceptable carrier" as used herein means a pharmaceutically-acceptable material, composition or vehicle, such as a liquid or solid filler, diluent, excipient, solvent or encapsulating material, involved in carrying or transporting a HPP from one location, body fluid, tissue, organ (interior or exterior), or portion of the body, to another location, body fluid, tissue, organ, or portion of the body.

Each carrier is "pharmaceutically acceptable" in the sense of being compatible with the other ingredients, e.g., a HPP, of the formulation and suitable for use in contact with the tissue or organ of a biological system without excessive toxicity, irritation, allergic response, immunogenicity, or other problems or complications, commensurate with a reasonable benefit/risk ratio.

Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) alcohol, such as ethyl alcohol and propane alcohol; (20) phosphate buffer solutions; and (21) other non-toxic compatible substances employed in pharmaceutical formulations such as acetone.

The pharmaceutical compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like.

In one embodiment, the pharmaceutically acceptable carrier is an aqueous carrier, e.g. buffered saline and the like. In certain embodiments, the pharmaceutically acceptable carrier is a polar solvent, e.g. acetone and alcohol.

The concentration of HPP in these formulations can vary widely, and will be selected primarily based on fluid volumes, viscosities, body weight and the like in accordance with the particular mode of administration selected and the biological system's needs. For example, the concentration can be 0.0001% to 100%, 0.001% to 50%, 0.01% to 30%, 0.1% to 10% wt.

The compositions of the invention can be administered for prophylactic, therapeutic, and/or hygienic use. Such administration can be topical, mucosal, e.g., oral, nasal, vaginal, rectal, parenteral, transdermal, subcutaneous, intramuscular, intravenous, via inhalation, ophthalmic and other convenient routes. The pharmaceutical compositions can be administered in a variety of unit dosage forms depending upon the method of administration. For example, unit dosage forms suitable for oral administration include powder, tablets, pills, capsules and lozenges.

Thus, a typical pharmaceutical composition for intravenous administration would be about $10^{-9}$ g to about 100 g, about $10^{-6}$ g to about 100 g, about 0.001 g to about 100 g, about 0.01 g to about 10 g, or about 0.01 g to about 1 g per subject per day. Dosages from about 0.01 mg, up to about 5 g, per subject per day may be used. Actual methods for preparing parenterally administrable compositions will be known or apparent to those skilled in the art and are described in more detail in such publications as Remington's Pharmaceutical Science, 15th ed., Mack Publishing Company, Easton, Pa. (1980).

III. Applications of HPPs i) Methods for Penetrating a Biological Barrier.

Another aspect of the invention relates to a method of using a composition of the invention in penetrating one or more biological barriers in a biological subject. The method comprises a step of administering to a biological subject a HPP or a mustard or mustard-related compound, or a pharmaceutical composition thereof. In one embodiment, a HPP exhibits more than about 50 times or higher, >about 100 times or higher, >about 200 time higher, >about 300 times or higher, >about 500 times or higher, >about 1,000 times or higher penetration rate through one or more biological barriers than its parent drug.

The term "biological barrier" as used herein refers to a biological layer that separates an environment into different spatial areas or compartments, which separation is capable of modulating (e.g. restricting, limiting, enhancing or taking no action in) the passing through, penetrating or translocation of substance or matter from one compartment/area to another. The different spatial areas or compartments as referred to herein may have the same or different chemical or biological environment(s). The biological layer as referred herein includes, but is not limited to, a biological membrane, a cell layer, a biological structure, an inner surface of subjects, organisms, organs or body cavities, an external surface of subjects, organisms, organs or body cavities, or any combination or plurality thereof.

Examples of a biological membrane include a lipid bilayer structure, eukaryotic cell membrane, prokaryotic cell membrane, and intracellular membrane (e.g., nucleus or organelle membrane, such as membrane or envelope of Golgi apparatus, rough and smooth endoplasmic reticulum (ER), ribosomes, vacuoles, vesicles, liposomes, mitochondria, lysosome, nucleus, chloroplasts, plastids, peroxisomes or microbodies).

The lipid bilayer referred to herein is a double layer of lipid-class molecules, including, but not limited to, phospholipids and cholesterol. In a particular embodiment, lipids for bilayer are amphiphilic molecules consisting of polar head groups and non-polar fatty acid tails. The bilayer is composed of two layers of lipids arranged so that their hydrocarbon tails face one another to form an oily core held together by the hydrophobic effect, while their charged heads face the aqueous solutions on either side of the membrane. In another particular embodiment, the lipid bilayer may contain one or more embedded protein and/or sugar molecule(s).

Examples of a cell layer include a lining of eukaryotic cells (e.g., epithelium, lamina propria and smooth muscle or muscularis mucosa (in gastrointestinal tract)), a lining of prokaryotic cells (e.g., surface layer or S-layer which refers to a two dimensional structure monomolecular layer composed of identical proteins or glycoproteins, specifically, an S-layer refers to a part of a cell envelope commonly found in bacteria and archaea), a biofilm (a structured community of microorganisms encapsulated within a self-developed polymeric matrix and adherent to a living or inert surface), and a plant cell layer (e.g., empidermis). The cells may be normal cells or pathological cells (e.g. disease cells, cancer cells).

Examples of biological structures include structures sealed by tight or occluding junctions which provide a barrier to the entry of toxins, bacteria and viruses, e.g. the blood milk barrier and the blood brain barrier (BBB). In particular, BBB is composed of an impermeable class of endothelium, which presents both a physical barrier through tight junctions adjoining neighboring endothelial cells and a transport barrier comprised of efflux transporters. The biological structure may also include a mixture of cells, proteins and sugars (e.g. blood clots).

Examples of the inner surface of subjects, organisms, organs or body cavities include buccal mucosa, esophageal mucosa, gastric mucosa, intestinal mucosa, olfactory mucosa, oral mucosa, bronchial mucosa, uterine mucosa and endometrium (the mucosa of the uterus, inner layer of the wall of a pollen grain or the inner wall layer of a spore), or a combination or plurality thereof.

Examples of the external surface of subjects, organisms, organs or body cavities include capillaries (e.g. capillaries in the heart tissue), mucous membranes that are continuous with skin (e.g. such as at the nostrils, the lips, the ears, the genital area, and the anus), outer surface of an organ (e.g. liver, lung, stomach, brain, kidney, heart, ear, eye, nose, mouth, tongue, colon, pancreas, gallbladder, duodenum, rectum stomach, colonrectum, intestine, vein, respiratory system, vascular, the anorectum and pruritus ani), skin, cuticle (e.g., dead layers of epidermal cells or keratinocytes or superficial layer of overlapping cells covering the hair shaft of an animal, a multi-layered structure outside the epidermis of many invertebrates, plant cuticles or polymers cutin and/or cutan), external layer of the wall of a pollen grain or the external wall layer of a spore), and a combination or plurality thereof.

In addition, a biological barrier further includes a sugar layer, a protein layer or any other biological layer, or a combination or plurality thereof. For example, skin is a biological barrier that has a plurality of biological layers. A skin comprises an epidermis layer (outer surface), a demis layer and a subcutaneous layer. The epidermis layer contains several layers including a basal cell layer, a spinous cell layer, a granular cell layer, and a stratum corneum. The cells in the epidermis are called keratinocytes. The stratum corneum ("horny layer") is the outmost layer of the epidermis, wherein cells here are flat and scale-like ("squamous") in shape. These cells contain a lot of keratin and are arranged in overlapping layers that impart a tough and oilproof and waterproof character to the skin's surface.

ii) Methods for Diagnosing a Condition in a Biological System.

Another aspect of the invention relates to a method of using a composition of the invention in diagnosing a condition in a biological system. The method comprises the following steps:

1) administrating a composition comprising a HPP of a mustard or mustard-related compound to the biological subject;

2) detecting the presence, location or amount of the HPP, the functional unit of the HPP or a metabolite thereof in the biological subject; and 3) determining a condition in the biological system.

In certain embodiments, the HPP (or the agent cleaved from the HPP) aggregates in the site of action where a condition occurs. In certain embodiments, the presence, location or amount of the functional unit of the HPP is also detected. In certain embodiments, the onset, development, progress, or remission of a condition (e.g., cancer) associated is also determined.

In certain embodiments, the HPP is labeled with or conjugated to a detectable agent. Alternatively, the HPP is prepared to include radioisotopes for detection. Numerous detectable agents are available which can be generally grouped into the following categories:

(a) Radioisotopes, such as $^{35}S$, $^{14}C$, $^{13}C$, $^{15}N$, $^{125}I$, $^{3}H$, and $^{131}I$. The diagnostic agent can be labeled with the radioisotope using the techniques known in the art and radioactivity can be measured using scintillation counting; in addition, the diagnostic agent can be spin labeled for electron paramagnetic resonance for carbon and nitrogen labeling.

(b) Fluorescent agents such as BODIPY, BODIPY analogs, rare earth chelates (europium chelates), fluorescein and its derivatives, FITC, 5,6 carboxyfluorescein, rhodamine and its derivatives, dansyl, Lissamine, phycoerythrin, green fluorescent protein, yellow fluorescent protein, red fluorescent protein and Texas Red. Fluorescence can be quantified using a fluorometer.

(c) Various enzyme-substrate agents, such luciferases (e.g., firefly luciferase and bacterial luciferase), luciferin, 2,3-dihydrophthalazinediones, malate dehydrogenase, urease, peroxidase such as horseradish peroxidase (HRPO), alkaline phosphatase, β-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like. Examples of enzyme-substrate combinations include, for example: (i) Horseradish peroxidase (HRPO) with hydrogen peroxidase as a substrate, wherein the hydrogen peroxidase oxidizes a dye precursor (e.g., orthophenylene diamine (OPD) or 3,3', 5,5'-tetramethyl benzidine hydrochloride (TMB)); (ii) alkaline phosphatase (AP) with para-Nitrophenyl phosphate as chromogenic substrate; and (iii) β-D-galactosidase (β-D-Gal) with a chromogenic substrate (e.g., p-nitrophenyl-β-D-galactosidase) or fluorogenic substrate 4-methylumbelliferyl-β-D-galactosidase.

In certain embodiments, the detectable agent is not necessarily conjugated to the diagnostic agent but is capable of recognizing the presence of the diagnostic agent and the diagnostic agent can be detected.

In certain embodiments, the HPP of the invention can be provided in a kit, i.e., a packaged combination of reagents in predetermined amounts with instructions for performing the diagnostic assay. Where the HPP is labeled with an enzyme, the kit will include substrates and cofactors required by the enzyme (e.g., a substrate precursor which provides the detectable chromophore or fluorophore). In addition, other additives may be included such as stabilizers, buffers (e.g., a block buffer or lysis buffer) and the like. The relative amounts of the various reagents may be varied widely to provide for concentrations in solution of the reagents which substantially optimize the sensitivity of the assay. Particularly, the reagents may be provided as dry powders, usually lyophilized, including excipients which on dissolution will provide a reagent solution having the appropriate concentration.

iii) Methods for Screening a Substance for a Desired Character

Another aspect of the invention relates to a method of screening a HPP for a desired character.

In certain embodiments, the method comprises:
1) covalently linking a test functional unit to a transportational unit through a linker to form a test composition (or covalently linking a functional unit to a test transportational unit through a linker, or covalently linking a functional unit to a transportational unit through a test linker)
2) administrating the test composition to a biological system; and
3) determining whether the test composition has the desired nature or character.

In one embodiment, a desired character may include, for example, 1) the ability of a test functional unit to form a high penetration composition or convert back to a parent drug, 2) the penetration ability and/or rate of a test composition, 3) the efficiency and/or efficacy of a test composition, 4) the transportational ability of a test transportational unit, and 5) the cleavability of a test linker.

iv) Methods for Treating a Condition in a Biological Subject

Another aspect of the invention relates to a method of using a composition of the invention in treating a condition in a biological system. The method comprises administrating the pharmaceutical composition to the biological system.

The term "treating" as used herein means curing, alleviating, inhibiting, or preventing. The term "treat" as used herein means cure, alleviate, inhibit, or prevent. The term "treatment" as used herein means cure, alleviation, inhibition or prevention.

The term "biological system," "biological subject" or "subject" as used herein means an organ, a group of organs that work together to perform a certain task, an organism, or a group of organisms. The term "organism" as used herein means an assembly of molecules that function as a more or less stable whole and has the properties of life, such as animal, plant, fungus, or micro-organism.

The term "animal" as used herein means an eukaryotic organism characterized by voluntary movement. Examples of animal include, without limitation, vertebrata (e.g. human, mammals, birds, reptiles, amphibians, fishes, marsipobranchiata and leptocardia), tunicata (e.g. thaliacea, appendicularia, sorberacea and ascidioidea), articulata (e.g. insecta, myriapoda, malacapoda, arachnida, pycnogonida, merostomata, crustacea and annelida), gehyrea (anarthropoda), and helminthes (e.g. rotifera).

The term "plant" as used herein means organisms belonging to the kindom Plantae. Examples of plant include, without limitation, seed plants, bryophytes, ferns and fern allies. Examples of seed plants include, without limitation, cycads, ginkgo, conifers, gnetophytes, angiosperms. Examples of bryophytes include, without limitation, liverworts, hornworts and mosses. Examples of ferns include, without limitation, ophioglossales (e.g. adders-tongues, moonworts, and grape-ferns), marattiaceae and leptosporangiate ferns. Examples of fern allies include, without limitation, lycopsida (e.g. clubmosses, spikemosses and quillworts), psilotaceae (e.g. lycopodiophyta and whisk ferns) and equisetaceae (e.g. horsetails).

The term "fungus" as used herein means a eukaryotic organism that is a member of the kingdom Fungi. Examples of fungus include, without limitation, chytrids, blastocladiomycota, neocallimastigomycota, zygomycota, glomeromycota, ascomycota and basidiomycota.

The term "micro-organism" as used herein means an organism that is microscopic (e.g. with length scale of micrometer), Examples of micro-organism include, without limitation, bacteria, fungi, archaea, protists and microscopic plants (e.g. green algae) and microscopic animals (e.g. plankton, planarian and amoeba).

Some examples of the conditions the method can treat include conditions that can be treated by the parent drug of the HPP.

v). Methods of Using HPPs of Mustards and Mustard-Related Compounds and Pharmaceutical Compositions Thereof in Treatments.

Another aspect of the invention relates to a method of using HPPs of mustards or mustard-related compounds, or pharmaceutical compositions thereof in treating a condition in a biological system or subject by administrating a HPP of a mustard or mustard-related compound, or a pharmaceutical compositions thereof to the biological system or subject.

Examples of the conditions that can be treated by the method include psoriasis and tumor, e.g., benign tumor, breast cancer, colon-rectum cancer, oral cancer, lung or other respiratory system cancers, skin cancers, uterus cancer, pancreatic cancer, prostate cancer, genital cancer, urinary organs cancers, leukemia or other blood and lymph tissues cancer.

In certain embodiments, a method of treating a condition in a subject amelioratable or treatable with mustards or mustard-related compounds comprises administering a therapeutic effective amount of a HPP of a mustard or mustard-related compound, or a pharmaceutical composition thereof to the subject.

A HPP or a pharmaceutical composition thereof can be administered to a biological system by any administration route known in the art, including without limitation, oral, enteral, buccal, nasal, topical, rectal, vaginal, aerosol, transmucosal, epidermal, transdermal, dermal, ophthalmic, pulmonary, subcutaneous, and/or parenteral administration. The pharmaceutical compositions can be administered in a variety of unit dosage forms depending upon the method of administration.

A parenteral administration refers to an administration route that typically relates to injection which includes but is not limited to intravenous, intramuscular, intraarterial, intrathecal, intracapsular, intraorbital, intra cardiac, intradermal, intraperitoneal, transtracheal, subcutaneous, subcuticular, intraarticular, subcapsular, subarachnoid, intraspinal, and/or intrasternal injection and/or infusion.

A HPP or a pharmaceutical composition thereof can be given to a subject in the form of formulations or preparations suitable for each administration route. The formulations useful in the methods of the invention include one or more HPPs, one or more pharmaceutically acceptable carriers therefor, and optionally other therapeutic ingredients. The formulations may conveniently be presented in unit dosage form and may be prepared by any methods well known in the art of pharmacy. The amount of active ingredient which can be combined with a carrier material to produce a single dosage form will vary depending upon the subject being treated and the particular mode of administration. The amount of a HPP which can be combined with a carrier material to produce a pharmaceutically effective dose will generally be that amount of a HPP which produces a therapeutic effect. Generally, out of one hundred percent, this amount will range from about 1 percent to about ninety-nine percent of the HPP, preferably from about 20 percent to about 70 percent.

Methods of preparing these formulations or compositions include the step of bringing into association a HPP with one or more pharmaceutically acceptable carriers and, optionally, one or more accessory ingredients. In general, the formulations are prepared by uniformly and intimately bringing into association a HPP with liquid carriers, or finely divided solid carriers, or both, and then, if necessary, shaping the product.

Formulations suitable for oral administration may be in the form of capsules, cachets, pills, tablets, lozenges (using a flavored basis, usually sucrose and acacia or tragacanth), powders, granules, or as a solution or a suspension in an aqueous or nonaqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a HPP as an active ingredient. A compound may also be administered as a bolus, electuary, or paste.

In solid dosage forms for oral administration (e. g., capsules, tablets, pills, dragees, powders, granules and the like), the HPP is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate, (5) solution retarding agents, such as paraffin, (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered peptide or peptidomimetic moistened with an inert liquid diluent. Tablets, and other solid dosage forms, such as dragees, capsules, pills and granules, may optionally be scored or prepared with coatings and shells, such as enteric coatings and other coatings well known in the pharmaceutical-formulating art. They may also be formulated so as to provide slow or controlled release of a HPP therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain pacifying agents and may be of a composition that they release the HPP(s) only, or preferentially, in a certain portion of the gastrointestinal tract, optionally, in a delayed manner. Examples of embedding compositions which can be used include polymeric substances and waxes. The HPP can also be in micro-encapsulated form, if appropriate, with one or more of the above-described excipients.

Liquid dosage forms for oral administration include pharmaceutically acceptable emulsions, microemulsions, solutions, suspensions, syrups and elixirs. In addition to the HPP, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, coloring, perfuming and preservative agents.

Suspensions, in addition to the HPP, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing one or more HPPs with one or more suitable non-irritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active agent. Formulations which are suitable for vaginal administration also include pessaries, tampons, creams, gels, pastes, foams or spray formulations containing such carriers as are known in the art to be appropriate.

Formulations for the topical or transdermal or epidermal or dermal administration of a HPP composition include powders, sprays, ointments, pastes, creams, lotions, gels, solutions, patches and inhalants. The active component may be mixed under sterile conditions with a pharmaceutically acceptable carrier, and with any preservatives, buffers, or propellants which may be required. The ointments, pastes, creams and gels may contain, in addition to the HPP composition, excipients, such as animal and vegetable fats, oils, waxes, paraffins, starch, tragacanth, cellulose derivatives, polyethylene glycols, silicones, bentonites, silicic acid, talc and zinc oxide, or mixtures thereof. Powders and sprays can contain, in addition to the HPP composition, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

A HPP or a pharmaceutical composition thereof can be alternatively administered by aerosol. This can be accomplished by preparing an aqueous aerosol, liposomal preparation or solid particles containing the HPPs. A nonaqueous (e. g., fluorocarbon propellant) suspension could be used. Sonic nebulizers can also be used. An aqueous aerosol is made by formulating an aqueous solution or suspension of the agent together with conventional pharmaceutically acceptable carriers and stabilizers. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Transdermal patches can also be used to deliver HPP compositions to an tumor site. Such formulations can be made by dissolving or dispersing the agent in the proper medium. Absorption enhancers can also be used to increase the flux of the peptidomimetic across the skin. The rate of such flux can be controlled by either providing a rate controlling membrane or dispersing the peptidomimetic in a polymer matrix or gel.

Ophthalmic formulations, eye ointments, powders, solutions and the like, are also contemplated as being within the scope of this invention.

Formulations suitable for parenteral administration comprise a HPP in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacterostats, solutes which render the formulation isotonic with the blood of the intended recipient or suspending or thickening agents.

Examples of suitable aqueous and nonaqueous carriers which may be employed in the formulations suitable for parenteral administration include water, ethanol, polyols (e. g., such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

Formulations suitable for parenteral administration may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Injectable depot forms are made by forming microencapsule matrices of a HPP or in biodegradable polymers such as polylactide-polyglycolide. Depending on the ratio of the HPP to polymer, and the nature of the particular polymer employed, the rate of drug release can be controlled. Examples of other biodegradable polymers include poly (orthoesters) and poly (anhydrides). Depot injectable formulations are also prepared by entrapping the HPP in liposomes or microemulsions which are compatible with body tissue.

In certain embodiments, a HPP of a mustard or mustard-related compound, or a pharmaceutical composition thereof is delivered to a disease or tumor site in a therapeutically effective dose. As is known in the art of pharmacology, the precise amount of the pharmaceutically effective dose of a HPP that will yield the most effective results in terms of efficacy of treatment in a given patient will depend upon, for example, the activity, the particular nature, pharmacokinetics, pharmacodynamics, and bioavailability of a particular HPP, physiological condition of the subject (including race, age, sex, weight, diet, disease type and stage, general physical condition, responsiveness to a given dosage and type of medication), the nature of pharmaceutically acceptable carriers in a formulation, the route and frequency of administration being used, and the severity or propensity of a disease caused by pathogenic target microbial organisms, to name a few. However, the above guidelines can be used as the basis for fine-tuning the treatment, e. g., determining the optimum dose of administration, which will require no more than routine experimentation consisting of monitoring the subject and adjusting the dosage. Remington: The Science and Practice of Pharmacy (Gennaro ed. 20.sup.th edition, Williams & Wilkins PA, USA) (2000).

IV. Advantages

In certain embodiments, since a HPP of the invention is capable of crossing one or more biological barriers, the HPP can be administered locally (e.g., topically or transdermally) to reach a location where a condition occurs without the necessity of a systematic administration (e.g., oral or parenteral administration). A local administration and penetration of a HPP allows the HPP to reach the same level of local concentration of an agent or drug with much less amount or dosage of HPP in comparison to a systematic administration of a parent agent or drug; alternatively, a higher level of local concentration which may not be afforded in the systematic administration, or if possible, requires significantly higher dosage of an agent in the systematic administration. The high local concentration of the HPP or its parent agent if being cleaved enables the treatment of a condition more effectively or much faster than a systematically delivered parent agent and the treatment of new conditions that may not be possible or observed before. The local administration of the HPP may allow a biological subject to reduce potential sufferings from a systemic administration, e.g., adverse reactions associated with the systematic exposure to the agent, gastrointestinal/renal effects. Additionally, the local administration may allow the HPP to cross a plurality of biological barriers and reach systematically through, for example, general circulation and thus avoid the needs for systematic administration (e.g., injection) and obviate the pain associated with the parenteral injection.

In certain embodiments, a HPP or a pharmaceutical composition according to the invention can be administered systematically (e.g., orally or parenterally). The HPP or the active agent (e.g., drug or metabolite) of the HPP may enter the general circulation with a faster rate than the parent agent and gain faster access to the action site a condition. Additionally, the HPP can cross a biological barrier (e.g., blood brain barrier) which has not been penetrated if a parent agent is administered alone and thus offer novel treatment of conditions that may not be possible or observed before.

For example, HPPs of mustards or mustard-related compounds in the invention demonstrated high penetration rate through a biological barrier (e.g., >about 10 times, >about 50 times, >about 100 times, >about 200 times, >about 300 times higher than if the mustards or mustard-related compounds are administered alone). No or few adverse side effect was observed from the subjects that took mustards HPP, while side effects (such as nausea, hair loss, and increased susceptibility to infection) were observed from the subjects that took the parent mustards at the similar dosage.

V. Examples

The following examples are provided to better illustrate the claimed invention and are not to be interpreted in any way as limiting the scope of the invention. All specific compositions, materials, and methods described below, in whole or in part, fall within the scope of the invention. These specific compositions, materials, and methods are not intended to limit the invention, but merely to illustrate specific embodiments falling within the scope of the invention. One skilled in the art may develop equivalent compositions, materials, and methods without the exercise of inventive capacity and without departing from the scope of the invention. It will be understood that many variations can be made in the procedures herein described while still remaining within the bounds of the invention. It is the intention of the inventors that such variations are included within the scope of the invention.

Example 1. Preparation of a HPP from a Parent Drug

Preparation of a HPP from a Parent Drug which Contains at Least One Carboxylic Group.

In certain embodiments, a parent compound having the following Structure C:

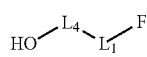

Structure C is converted to a HPP having Structure L:

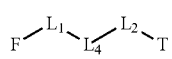

Structure L including stereoisomers and pharmaceutically acceptable salts thereof, wherein:

F, $L_1$, $L_2$, $L_4$ and T are defined the same as supra;

In certain embodiments of the invention, a HPP having Structure L is prepared according to the conventional organic synthesis by reacting the parent compounds or derivatives of the parent compounds having Structure D (e.g. acid halides, mixed anhydrides of the parent compounds, etc.):

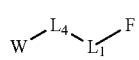

Structure D with compounds of Structure E (Scheme 1):

Structure E wherein W is selected from the group consisting of OH, halogen, alkoxycarbonyl and substituted aryloxycarbonyloxy; and F, T, $L_1$, $L_2$, and $L_4$ are defined the same as supra.

Scheme 1. Preparation of a HPP from a parent compound.

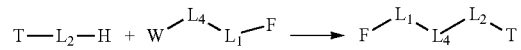

In certain embodiments, a HPP having Structure L is prepared following Scheme 1 as described supra, wherein $L_4$ is C=O.

Preparation of N,N-diethylaminoethyl 4-[bis(2-chloroethyl) amino] benzenebutyrate.HBr 32.6 g (0.1 mol) of sodium 4-[bis(2-chloroethyl)amino] benzenebutyrate was dissolved in 100 ml of acetonitrile. 26 g (0.10 mol) of 2-Bromo-N,N-diethylethylamine.HBr in ethyl acetate was added into the reaction mixture. The mixture was stirred for 3 h at RT. Solid is removed by filtration. The solvents were evaporated off. The solid product was collected by filtration and washed with ether. After drying, it yielded 35 g of the desired product (72.3%). Hygroscopic product; Solubility in water: 300 mg/ml; Elementary analysis: $C_{20}H_{33}BrCl_2N_2O_2$; MW: 484.30. Calculated % C: 49.60, H: 6.87, Br: 16.50, N: 5.78, O: 6.61; Cl: 14.64; Found % C: 49.52, H: 6.89, Br: 16.55 N: 5.75, O: 6.65; Cl: 14.64. $^1$H-NMR (400 MHz, $D_2O$): δ: 1.55 (t, 6H), 2.02 (m, 2H), 2.27 (m, 2H), 2.54 (m, 2H), 3.23 (m, 4H), 3.51 (m, 2H), 3.60-3.65 (m, 8H), 4.51 (m, 2H), 6.55 (m, 2H), 6.95 (m, 2H).

Preparation of N,N-diethylaminoethyl 4-[bis(2-chloroethyl) amino] benzenebutyrate.HCl (A) 30.4 g (0.1 mol) of 4-[bis(2-chloroethyl)amino]benzenebutanoic acid was dissolved in 300 ml of chloroform. 20.6 g of N, N'-Dicyclohexylcarbodiimide was added into the reaction mixture. 11.7 g of N,N-diethylaminoethanol and 0.2 g of 4-dimethylaminopyridine were added into the reaction mixture. The mixture was stirred overnight at 0° C. The solid was removed by filtration. The chloroform solution was washed with water (1×100 ml), 5% NaHCO$_3$ (1×100 ml) and water (3×100 ml). The organic solution was dried over anhydrous sodium sulfate. Sodium sulfate was removed by filtration. 4 g of HCl gas in methanol (10 ml) was added into the reaction mixture with stirring. Hexane (200 ml) was added. The solid product was collected by filtration. After drying, it yielded 35 g of the desired product (79.6%). Hygroscopic product; Solubility in water: 300 mg/ml; Elementary analysis: $C_{20}H_{33}Cl_3N_2O_2$; MW: 439.85. Calculated % C: 54.61, H: 7.56, N: 6.37; O: 7.27; Cl: 24.18; Found % C: 54.55; H: 7.58; N: 6.34, O: 7.29; Cl: 24.24. 1H-NMR (400 MHz, D2O): δ: 1.56 (t, 6H), 2.01 (m, 2H), 2.25 (m, 2H), 2.55 (m, 2H), 3.22 (m, 4H), 3.52 (m, 2H), 3.60-3.65 (m, 8H), 4.50 (m, 2H), 6.55 (m, 2H), 6.95 (m, 2H).

(B) 60.8 g (0.1 mol) of 4-[bis(2-chloroethyl)amino]benzenebutanoic acid was dissolved in 300 ml of chloroform. 20.6 g of N, N'-Dicyclohexylcarbodiimide was added into the reaction mixture. 11.7 g of N,N-diethylaminoethanol was added into the reaction mixture. The mixture was stirred overnight at 0° C. The solid was removed by filtration. The chloroform solution was washed with water (1×100 ml), 5%

NaHCO$_3$ (1×100 ml) and water (3×100 ml). The organic solution was dried over anhydrous sodium sulfate. Sodium sulfate was removed by filtration. 4 g of HCl gas in methanol (10 ml) was added into the reaction mixture with stirring. Hexane (200 ml) was added. The solid product was collected by filtration. After drying, it yielded 32 g of the desired product (73%). Hygroscopic product; Elementary analysis: C$_{20}$H$_{33}$Cl$_3$N$_2$O$_2$; MW: 439.85. Calculated % C: 54.61, H: 7.56, N: 6.37; O: 7.27; Cl: 24.18; Found % C: 54.57; H: 7.57; N: 6.34, O: 7.29; Cl: 24.23.

Preparation of 4-[bis(2-chloroethyl)amino]-N-acetyl-L-phenylalanine N,N-diethylaminoethyl ester hydrobromide 36.9 g (0.1 mol) of sodium 4-[bis(2-chloroethyl)amino]-N-acetyl-L-phenylalanine was dissolved in 100 ml of acetonitrile. 26 g (0.10 mol) of 2-Bromo-N,N-diethylethyl-amine.HBr in ethyl acetate was added into the reaction mixture. The mixture was stirred for 3 h at RT. Solid is removed by filtration. The solvents were evaporated off. The solid product was collected by filtration and washed with ether. After drying, it yielded 38 g of the desired product (72.1%). Hygroscopic product; Solubility in water: 300 mg/ml; Elementary analysis: C$_{21}$H$_{34}$BrCl$_2$N$_2$O$_2$; MW: 527.32. Calculated % C: 47.83, H: 6.50, Br: 15.15, N: 7.97, O: 9.10, Cl: 13.45; Found % C: 47.77, H: 6.52, Br: 15.12 N: 7.96, O: 9.15; Cl: 13.48. $^1$H-NMR (400 MHz, D$_2$O): δ: 1.54 (t, 6H), 2.02 (s, 3H), 3.16 (m, 2H), 3.23 (m, 4H), 3.51 (m, 2H), 3.60-3.65 (m, 8H), 4.51 (m, 2H), 4.81 (m, 1H), 6.55 (m, 2H), 6.95 (m, 2H).

Example 2. HPPs of Mustards and Mustard-Related Compounds have Higher in Vitro Penetration Rates Across Human Skin Comparing to their Parent Drugs The penetration rates of HPPs and their parent drugs through human skin were measured in vitro by modified Franz cells. The Franz cells had two chambers, the top sample chamber and the bottom receiving chamber. The human skin tissue (360-400 μm thick) that separated the top and the receiving chambers was isolated from the anterior or posterior thigh areas.

The compound tested (2 mL, 20% in 0.2 M phosphate buffer, pH. 7.4) were added to the sample chamber of a Franz cell. The receiving chamber contains 10 ml of 2% bovine serum albumin in saline which was stirred at 600 rpm. The amount of the tested compound penetrating the skin was determined by high-performance liquid chromatography (HPLC) method. The results were shown in FIG. 1. The apparent flux values of the tested compounds were calculated from the slopes in FIG. 1 and summarized in Table 1.

Because the lowest detectable apparent flux values in this method was 1 μg/cm$^2$/h, parent drugs that showed a apparent flux value less than 1 μg/cm$^2$/h were considered as not detectable for penetrating across the skin tissue. The HPPs of these parent drugs (e.g. nitrogen mustards, nitrobenzyl mustards, phosphoramide mustard, isophosphoramide mustards and aldophosphamide) had detectable penetration across the skin tissue. For the parent drugs that had detectable apparent flux value, their HPPs had higher apparent flux value.

TABLE 1

In vitro Penetration Rate of HPPs and their Parent Compounds

| HPPs | mg/cm$^2$/h | Parent compounds | mg/cm$^2$/h |
|---|---|---|---|
| N,N-diethylaminoethyl 4-[bis(2-chloroethyl)amino]benzenebutyrate•HBr | 1.01 | chlorambucil | 0.01 |
| 4-[bis(2-chloroethyl)amino]-N-acetyl-L-phenylalanine N,N-diethylaminoethyl ester hydrobromide | 1.10 | melphalan | 0.01 |
| N,N-bis(2-chloroethyl)aminophosphamide N,N-diethylaminoethyl ester hydrobromide | 0.85 | N,N-bis(2-chloroethyl)aminophosphamide | 0.01 |
| diethylaminoethyl 4-[bis(2-methylsulfonylethyl)amino]benzenebutyrate•HBr | 0.94 | 4-[bis(2-methylsulfonylethyl)amino]benzenebutanoic acid | 0.01 |

Example 3. In Vivo Transportation of Prodrug and Application of HPPs of Mustards and Mustard-Related Compounds in Treating Cancer 1) Blocking Human Gastric Cancer HGC-27 Cell Proliferation with Chlorambucil and N,N-diethylaminoethyl 4-[bis(2-chloroethyl)amino]benzenebutyrate The inhibition of cellular proliferation was measured by the modified dimethyl thiazolyl diphenyl tetrazolium salt (MTT) [3-(4,5-dimethylthiazol-2-yl)-2,5-diphenyltetrazolium bromide] assay, based on the ability of live cells to converting thiazolyl blue to dark blue formazan. Approximately 3500 cells of HGC-27 (in 100 μl culture solution) were seeded into 96-well culture plates and were cultured for 16 hours at 37° C. Different concentration solution (100 μl) of Taxol (positive control), chlorambucil, or N,N-diethylaminoethyl 4-[bis(2-chloroethyl) amino]benzenebutyrate were added and incubation continued for 72 hours at 37° C. Then MTT were added and incubation continued at 37° C. for 4 h, and 100 μl DMSO was pipetted to solubilize the formazan product for 30 min at room temperature. The absorbency at 570 nm was measured using Bio-Rad microplate reader stored at −20° C. until use for electrophoresis. EC$_{50}$ were calculated with the software Prism Graphpad.

Results: HGC-27 cell growth inhibition rates for chlorambucil at the final concentrations of 500, 200, 100, 75, 50, 25, 5, 2, 0.5 μm were 81.0%, 47.7%, 39.2%, 34.2%, 34.9%, 25.0%, 1.6%, 0.3% and EC50 is >100 μm. HGC-27 cell growth inhibition rates for N,N-diethylaminoethyl 4-[bis(2-chloroethyl)amino]benzenebutyrate at the final concentrations of 500, 200, 100, 75, 50, 25, 5, 2, 0.5 μm were 94.8%. 94.8%, 94.7%, 93.4%, 81.6%, 54.6%, 46.9%, 34.7%, 25.5%, EC50 was <6 μM. HGC-27 cell growth inhibition rates for taxol at the final concentrations of 5000 nm, 500 nm, 100 nm, 50 nm, 25 nm, 10 nm, 1 nm, 0.5 nm were 95.8%, 94.7%, 92.2%, 85.2%, 76.9%, 45.0%, 21.6%, 10.3% and EC50 was ~13 nm.

2) For Evaluation of Antitumor Activity, a Human Myeloma Cell Line Derived from the Ascites of a Patient with Multiple Myeloma was Implanted into Mice.

The experiment was carried out on 11 groups of mice. Control group (A, orally), melphalan (B$_1$ and B$_2$, orally), chlorambucil (C$_1$ and C$_2$, orally), N,N-diethylaminoethyl 4-[bis(2-chloroethyl)amino]benzenebutyrate.HBr (D$_1$ and D$_2$, transdermally), 4-[bis(2-chloroethyl)amino]-N-acetyl-L-phenylalanine N,N-diethylaminoethyl ester hydrobromide (E$_1$ and E$_2$, transdermally), and diethylaminoethyl 4-[bis(2-methylsulfonylethyl)amino]benzenebutyrate.HCl ($F_1$ and $F_2$, transdermally). The body weight loss of mice was determined on day 21. The results were shown in Table 2.

TABLE 2

Extension of survival period and weight loss of cancer mice by use of mustards and their novel prodrugs.

| Compounds | Dose (mg/kg) perday | n | Survival Period (days) | Life Elongation Rate(%) | None Disease Rate | Weight Loss (%) |
|---|---|---|---|---|---|---|
| Control (A) | — | 7 | 45.5 ± 1.6 | 100 | 0/7 | 1% |
| B | 1.5 mg | 7 | 55.7 ± 1.3 | 122 | 0/7 | 10% |
| B | 3 mg | 7 | 88.5 ± 1.8 | 195 | 2/7 | 18% |
| $C_1$ | 1.5 mg | 7 | 57.8 ± 1.5 | 127 | 2/7 | 9% |
| $C_2$ | 3 mg | 7 | 90.2 ± 1.9 | 198 | 3/7 | 17% |
| $D_1$ | 1.5 mg | 7 | 128.5 ± 1.3 | 282 | 4/7 | 5% |
| $D_2$ | 3 mg | 7 | 115.2 ± 2.1 | 253 | 4/7 | 10% |
| $E_1$ | 1.5 mg | 7 | 130.5 ± 1.6 | 287 | 4/7 | 4% |
| $E_2$ | 3 mg | 7 | 121.2 ± 1.8 | 266 | 3/7 | 9% |
| $F_1$ | 1.5 mg | 7 | 122.5 ± 1.7 | 269 | 4/7 | 6% |
| $F_2$ | 3 mg | 7 | 111.2 ± 1.9 | 244 | 3/7 | 11% |

The results showed that the prodrugs demonstrated strong antitumor activity at 1.5 mg/kg dose and caused much less side effects (less weight loss) when they were administered transdermally.

What is claimed is:

1. A high penetration compound having the following chemical structure:

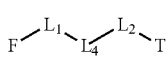

Structure L including stereoisomers and pharmaceutically acceptable salts thereof, wherein:

T is selected the group consisting of Structure Na, Structure Nb, Structure Nc, Structure Ne, Structure Ng, Structure Nh, and Structure Nm:

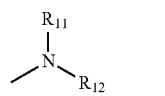

Structure Na

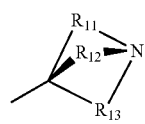

Structure Nb

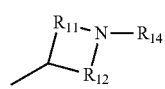

Structure Nc

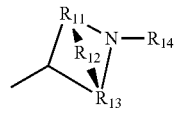

Structure Ne

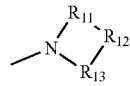

Structure Ng

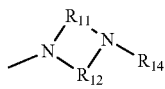

Structure Nh

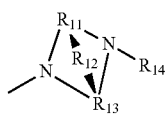

Structure Nm wherein:

$R_{11}$ and $R_{12}$ in Structure Na are same or different and each independently selected from H, substituted and unsubstituted alkyl, substituted and unsubstituted cycloalkyl, substituted and unsubstituted heterocycloalkyl, substituted and unsubstituted aryl, substituted and unsubstituted heteroaryl;

$R_{11}$, $R_{12}$ and $R_{13}$ in Structure Nb, Structure Nc, Structure Ng or Structure Nh are each independently substituted or unsubstituted alkylene;

$R_{11}$ and $R_{13}$ in Structure Ne and Structure Nm are each independently substituted or unsubstituted methine, and $R_{12}$ is substituted or unsubstituted alkylene;

each $R_{14}$ is selected from H, substituted and unsubstituted alkyl, substituted and unsubstituted cycloalkyl, substituted and unsubstituted heterocycloalkyl, substituted and unsubstituted aryl, substituted and unsubstituted heteroaryl;

$L_1$ is selected from the group consisting of a bond, O, S, —N($L_3$)-, —N($L_3$)-$CH_2$—O, —N($L_3$)-$CH_2$—N($L_3$)-, —O—$CH_2$—O—, —O—CH($L_3$)-O, and —S—CH($L_3$)-O—;

$L_2$ is selected from the group consisting of a bond, O, S, —N($L_3$)-, —N($L_3$)-$CH_2$—O, —N($L_3$)-$CH_2$—N($L_3$)-, —O—$CH_2$—O—, —O—CH($L_3$)-O, —S—CH($L_3$)-O—, —O-$L_5$-, —N-$L_5$-, —S-$L_5$-, —N($L_3$)-$L_5$-;

$L_4$ is C=O or C=S;

each $L_3$ is independently selected from the group consisting of H, substituted and unsubstituted alkyl, substituted and unsubstituted cycloalkyl, substituted and unsubstituted heterocycloalkyl, substituted and unsubstituted aryl, and substituted and unsubstituted heteroaryl;

each $L_5$ is independently selected from the group consisting of substituted and unsubstituted alkyl ene, substituted and unsubstituted cycloalkylene, substituted and unsubstituted heterocycloalkylene, substituted and unsubstituted arylene, and substituted and unsubstituted heteroarylene;

F comprises a moiety of a nitrogen mustard compound, having a structure of Structure A:

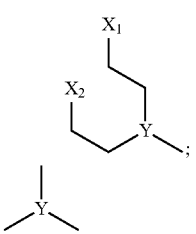

Structure A is selected from the group consisting of Structure Y-a, Structure Y-b, and Structure Y-c:

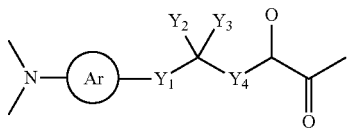
Structure Y-a

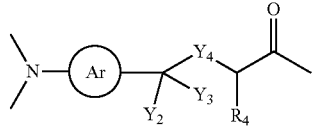
Structure Y-b

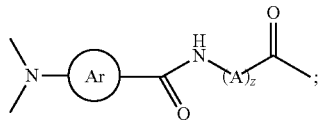
Structure Y-c

is selected from the group consisting of substituted and unsubstituted aryl, Structure Ar-a, Structure Ar-b, Structure Ar-c, Structure Ar-d, Structure Ar-e, Structure Ar-f, Structure Ar-g, Structure Ar-h and Structure Ar-i:

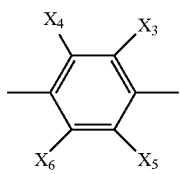
Structure Ar-a

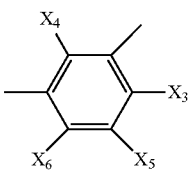
Structure Ar-b

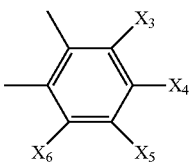
Structure Ar-c

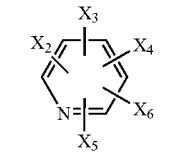
Structure Ar-d

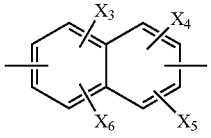
Structure Ar-e

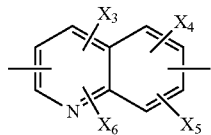
Structure Ar-f

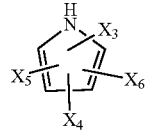
Structure Ar-g

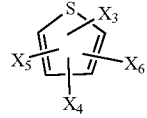
Structure Ar-h

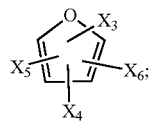
Structure Ar-i $X_1$ and $X_2$ are independently selected from the group consisting of Cl, Br, F, and $OSO_2R_4$;

$R_4$ is selected from the group consisting of unsubstituted alkyl, substituted and unsubstituted alkoxyl, substituted and unsubstituted perfluoroalkyl, substituted and unsubstituted alkyl halide, substituted and unsubstituted aryl, and substituted and unsubstituted heteroaryl groups;

$X_3$-$X_7$ are independently selected from the group consisting of $NHCOR_4$, $OR_4$, $SR_4$, $NHR_4$, $OCOR_4$, $R_4$, substituted and unsubstituted alkoxyl, substituted and unsubstituted alkylthio, substituted and unsubstituted alkylamino, substituted and unsubstituted alkyl halide, H, F, Cl, Br, I, $NO_2$, CN, $CF_3$, $NHCOCH_3$, $OCH_3$, $SCH_3$, $NH_2$, $NHCH_3$, $OCOCH_3$, $OCOC_2H_5$, $OC_2H_5$, $OC_3H_7$, $CH_3$, $C_2H_5$, and $C_3H_7$;

z is an integer;

$Y_1$ is selected from the group consisting of $CH_2$, O, S, and NH;

$Y_2$ and $Y_3$ are the same or different and each is $NHCOR_4$, H, OH, $NHCOCH_3$, $NHCOC_2H_5$, Cl, F, Br, or I, or taken together is =O;

$Y_4$ is selected from the group consisting of $R_4$, $CH_2$, —$(CH_2)_n$—, O, S, and NH;

A is selected from the group consisting of amino acids, α-amino acids and (β-amino acids residues;

any $CH_2$ groups may be replaced with O, S, or NH; and when a bond is not linked with any atom of an aryl or heteroaryl ring, the bond can be put into any position of the ring.

2. A high penetration compound comprising Structure 1, including stereoisomers, and pharmaceutically acceptable salts thereof, wherein: Structure 1 is selected from the group consisting of Structure 1a, Structure 1b, Structure 1c, Structure 1d, Structure 1e, Structure 1g, and Structure 1m:

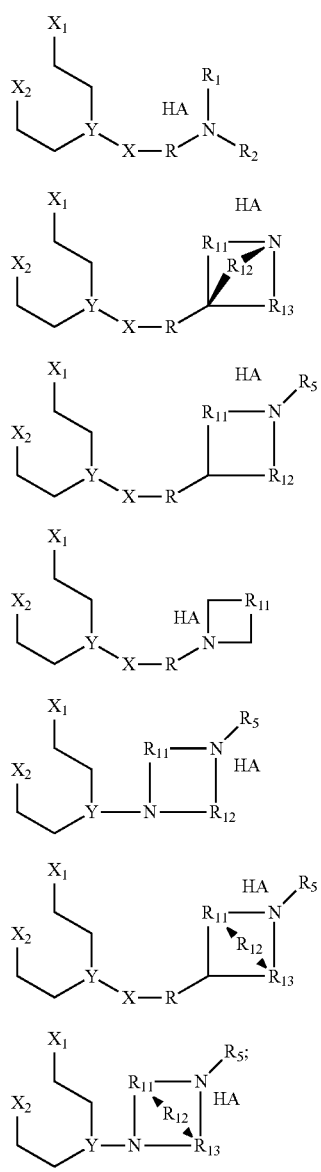
wherein, in any of Structure 1a, Structure 1b, Structure 1c, Structure 1d, Structure 1e, Structure 1g, and Structure 1m,
is selected from Structure Y-a, Structure Y-b, and Structure Y-c:
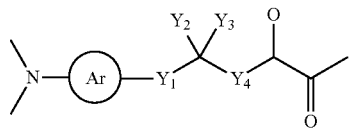
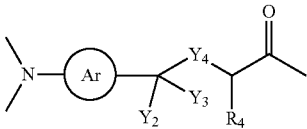
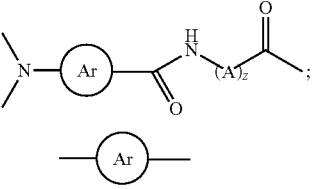
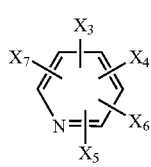
is selected from substituted and unsubstituted aryl, Structure Ar-a, Structure Ar-b, Structure Ar-c, Structure Ar-d, Structure Ar-e, Structure Ar-f, Structure Ar-g, Structure Ar-h and Structure Ar-i:
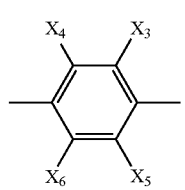
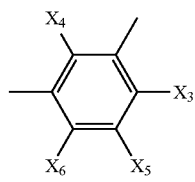
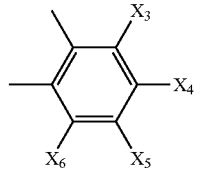
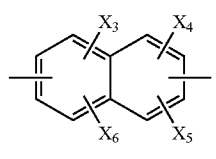
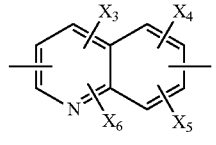

-continued

Structure Ar-g

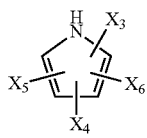

Structure Ar-h

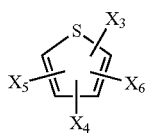

Structure Ar-i

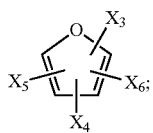

R$_4$ is selected from unsubstituted alkyl, substituted and unsubstituted alkoxyl, substituted and unsubstituted perfluoroalkyl, substituted and unsubstituted alkyl halide, substituted and unsubstituted aryl, and substituted and unsubstituted heteroaryl groups;

X$_3$-X$_4$ are independently selected from NHCOR$_5$, OR$_5$, SR$_5$, NHR$_5$, OCOR$_5$, R$_5$, substituted and unsubstituted alkoxyl, substituted and unsubstituted alkylthio, substituted and unsubstituted alkylamino, substituted and unsubstituted alkyl halide, H, F, Cl, Br, I, NO$_2$, CN, CF$_3$, NHCOCH$_3$, OCH$_3$, SCH$_3$, NH$_2$, NHCH$_3$, OCOCH$_3$, OCOC$_2$H$_5$, OC$_2$H$_5$, OC$_3$H$_7$, CH$_3$, C$_2$H$_5$, and C$_3$H$_7$;

X$_5$-X$_7$ are independently selected from NHCOR$_4$, OR$_4$, SR$_4$, NHR$_4$, OCOR$_4$, R$_4$, substituted and unsubstituted alkoxyl, substituted and unsubstituted alkylthio, substituted and unsubstituted alkylamino, substituted and unsubstituted alkyl halide, H, F, Cl, Br, I, NO$_2$, CN, CF$_3$, NHCOCH$_3$, OCH$_3$, SCH$_3$, NH$_2$, NHCH$_3$, OCOCH$_3$, OCOC$_2$H$_5$, OC$_2$H$_5$, OC$_3$H$_7$, CH$_3$, C$_2$H$_5$, and C$_3$H$_7$;

z is an integer;

Y$_1$ is selected from CH$_2$, O, S, and NH;

Y$_2$ and Y$_3$ are the same or different and each is NHCOR$_4$, H, OH, NHCOCH$_3$, NHCOC$_2$H$_5$, Cl, F, Br, or I, or taken together is =O;

Y$_4$ is selected from R$_4$, CH$_2$, —(CH$_2$)$_n$—, O, S, and NH;

A is selected from amino acids, α-amino acids and β-amino acids residues;

any CH$_2$ groups may be replaced with O, S, or NH; and when a bond is not linked with any atom of an aryl or heteroaryl ring, the bond can be put into any position of the ring;

R is independently selected from the group consisting of substituted and unsubstituted 0-20 carbon atoms alkylene, substituted and unsubstituted 1-20 carbon atoms perfluoroalkylene, substituted and unsubstituted 2-20 carbon atoms alkenylene, substituted and unsubstituted 2-20 carbon atoms alkynylene, substituted and unsubstituted 6-20 carbon atoms arylene, and substituted and unsubstituted 2-20 carbon atoms heteroarylene;

R$_1$ and R$_2$ in Structure 1a are same or different and each independently selected from H, substituted and unsubstituted alkyl, substituted and unsubstituted cycloalkyl, substituted and unsubstituted heterocycloalkyl, substituted and unsubstituted aryl, substituted and unsubstituted heteroaryl;

R$_{11}$, and R$_{12}$ in Structure 1b and Structure 1c are each independently substituted or unsubstituted alkylene;

R$_{13}$ in Structure 1b are each independently substituted or unsubstituted alkylene;

R$_5$ in Structure 1c, Structure 1e, Structure 1g, and Structure 1m is selected from H, substituted and unsubstituted alkyl, substituted and unsubstituted cycloalkyl, substituted and unsubstituted heterocycloalkyl, substituted and unsubstituted aryl, substituted and unsubstituted heteroaryl;

R$_{11}$ and R$_{13}$ in Structure 1g and Structure 1m are each independently substituted or unsubstituted methine, and R$_{12}$ is substituted or unsubstituted alkylene;

X is selected from the group consisting of O, S, NR$_5$, and NH;

X$_1$ and X$_2$ are independently selected from the group consisting of Cl, Br, F, and OSO$_2$R$_5$; and HA is selected from the group consisting of nothing, hydrochloride, hydrobromide, hydroiodide, nitric acid, sulfic acid, bisulfic acid, phosphoric acid, phosphorous acid, phosphonic acid, isonicotinic acid, acetic acid, lactic acid, salicylic acid, citric acid, tartaric acid, pantothenic acid, bitartaric acid, ascorbic acid, succinic acid, maleic acid, gentisinic acid, fumaric acid, gluconic acid, glucaronic acid, saccharic acid, formic acid, benzoic acid, glutamic acid, methanesulfonic acid, ethanesulfonic acid, benzensulfonic acid, p-toluenesulfonic acid and pamoic acid.

3. A pharmaceutical composition comprising a high penetration compound according to claim 1 and a pharmaceutically acceptable carrier.

4. The pharmaceutical composition according to claim 3, wherein the pharmaceutically acceptable carrier is polar.

5. The pharmaceutical composition according to claim 3, wherein the pharmaceutically acceptable carrier is selected from the group of alcohol, acetone, ester, water, and aqueous solution.

6. A high penetration compound having the following structure:

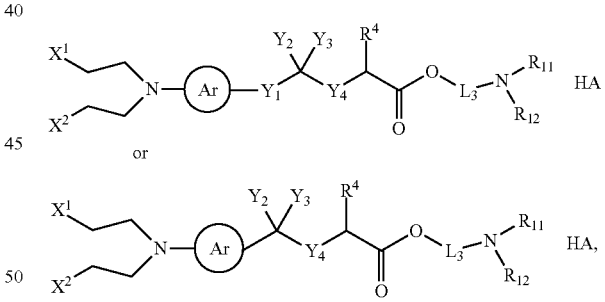

wherein:

X$_1$ and X$_2$ are independently selected from the group consisting of Cl, Br, F, and OSO$_2$R$_4$;

R$_4$ is selected from the group consisting of substituted and unsubstituted alkyl, substituted and unsubstituted alkoxyl, substituted and unsubstituted perfluoroalkyl, substituted and unsubstituted alkyl halide, substituted and unsubstituted aryl, and substituted and unsubstituted heteroaryl groups;

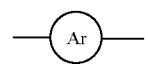

is selected from the group consisting of substituted and unsubstituted aryl, Structure Ar-a, Structure Ar-b, Structure Ar-c, Structure Ar-d, Structure Ar-e, Structure Ar-f, Structure Ar-g, Structure Ar-h and Structure Ar-i:

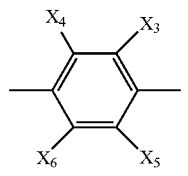
Structure Ar-a

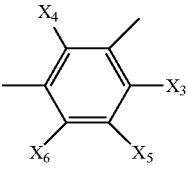
Structure Ar-b

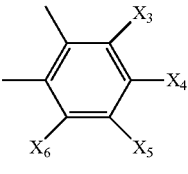
Structure Ar-c

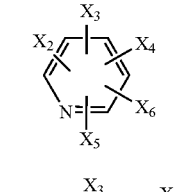
Structure Ar-d

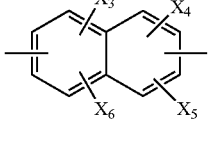
Structure Ar-e

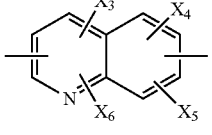
Structure Ar-f

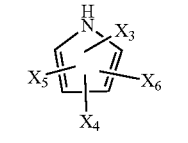
Structure Ar-g

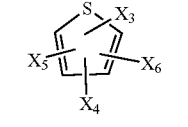
Structure Ar-h

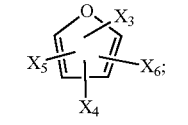
Structure Ar-i $X_3$-$X_7$ are independently selected from the group consisting of $NHCOR_4$, $OR_4$, $SR_4$, $NHR_4$, $OCOR_4$, $R_4$, substituted and unsubstituted alkoxyl, substituted and unsubstituted alkylthio, substituted and unsubstituted alkylamino, substituted and unsubstituted alkyl halide, H, F, Cl, Br, I, $NO_2$, CN, $CF_3$, $NHCOCH_3$, $OCH_3$, $SCH_3$, $NH_2$, $NHCH_3$, $OCOCH_3$, $OCOC_2H_5$, $OC_2H_5$, $OC_3H_7$, $CH_3$, $C_2H_5$, and $C_3H_7$;

$Y_1$ is selected from the group consisting of $CH_2$, O, S, and NH;

$Y_2$ and $Y_3$ are the same or different and each is $NHCOR_4$, H, OH, $NHCOCH_3$, $NHCOC_2H_5$, Cl, F, Br, or I, or taken together is =O;

$Y_4$ is selected from the group consisting of $R_4$, $CH_2$, —$(CH_2)_n$—, O, S, and NH;

$L_3$ is an alkylene;

$R_{11}$ and $R_{12}$ are independently selected from the group consisting of H, substituted and unsubstituted alkyl, substituted and unsubstituted cycloalkyl, substituted and unsubstituted heterocycloalkyl, substituted and unsubstituted aryl, substituted and unsubstituted heteroaryl; and HA is selected from the group consisting of nothing, hydrochloride, hydrobromide, hydroiodide, nitric acid, sulfic acid, bisulfic acid, phosphoric acid, phosphorous acid, phosphonic acid, isonicotinic acid, acetic acid, lactic acid, salicylic acid, citric acid, tartaric acid, pantothenic acid, bitartaric acid, ascorbic acid, succinic acid, maleic acid, gentisinic acid, fumaric acid, gluconic acid, glucaronic acid, saccharic acid, formic acid, benzoic acid, glutamic acid, methanesulfonic acid, ethanesulfonic acid, benzensulfonic acid, p-toluenesulfonic acid and pamoic acid.

7. The high penetration compound of claim 6, having the following structure:

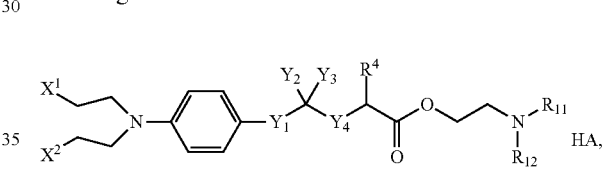

wherein:

$X_1$ and $X_2$ are independently selected from the group consisting of Cl and $OSO_2R_4$;

$R_4$ is selected from the group consisting of substituted and unsubstituted alkyl;

is selected from the group consisting of Structure Ar-a, Structure Ar-b, and Structure Ar-c:

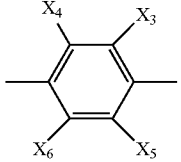
Structure Ar-a

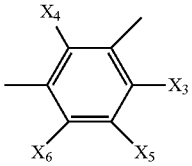
Structure Ar-b

-continued

Structure Ar-c

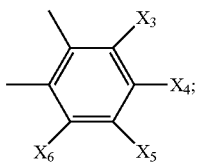

$X_3$-$X_6$ are independently selected from the group consisting of $NHCOR_4$, $OR_4$, $SR_4$, $NHR_4$, $OCOR_4$, $R_4$, substituted and unsubstituted alkoxyl, substituted and unsubstituted alkylthio, substituted and unsubstituted alkylamino, substituted and unsubstituted alkyl halide, H, F, Cl, Br, I, $NO_2$, CN, $CF_3$, $NHCOCH_3$, $OCH_3$, $SCH_3$, $NH_2$, $NHCH_3$, $OCOCH_3$, $OCOC_2H_5$, $OC_2H_5$, $OC_3H_7$, $CH_3$, $C_2H_5$, and $C_3H_7$;

$Y_1$ is selected from the group consisting of $CH_2$, O, S, and NH;

$Y_2$ and $Y_3$ are the same or different and each is $NHCOR_4$, H, OH, $NHCOCH_3$, $NHCOC_2H_5$, Cl, F, Br, or I, or taken together is =O;

$Y_4$ is selected from the group consisting of $R_4$, $CH_2$, —$(CH_2)_n$—, O, S, and NH;

$L_3$ is an alkylene;

$R_{11}$ and $R_{12}$ are independently selected from the group consisting of H and substituted and unsubstituted alkyl; and HA is selected from the group consisting of nothing, hydrochloride, hydrobromide, hydroiodide, nitric acid, sulfic acid, bisulfic acid, phosphoric acid, phosphorous acid, phosphonic acid, isonicotinic acid, acetic acid, lactic acid, salicylic acid, citric acid, tartaric acid, pantothenic acid, bitartaric acid, ascorbic acid, succinic acid, maleic acid, gentisinic acid, fumaric acid, gluconic acid, glucaronic acid, saccharic acid, formic acid, benzoic acid, glutamic acid, methanesulfonic acid, ethanesulfonic acid, benzensulfonic acid, p-toluenesulfonic acid and pamoic acid.

8. The high penetration compound of claim 6, having the following structure:

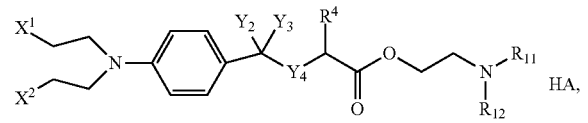

wherein:
$X_1$ and $X_2$ are independently selected from the group consisting of Cl and $OSO_2R_4$;
$R_4$ is selected from the group consisting of substituted and unsubstituted alkyl;

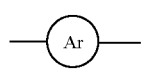

is selected from the group consisting of Structure Ar-a, Structure Ar-b, and Structure Ar-c:

Structure Ar-a

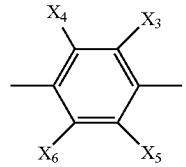

Structure Ar-b

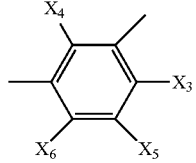

Structure Ar-c

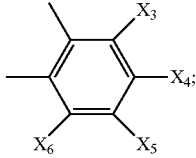

$X_3$-$X_6$ are independently selected from the group consisting of $NHCOR_4$, $OR_4$, $SR_4$, $NHR_4$, $OCOR_4$, $R_4$, substituted and unsubstituted alkoxyl, substituted and unsubstituted alkylthio, substituted and unsubstituted alkylamino, substituted and unsubstituted alkyl halide, H, F, Cl, Br, I, $NO_2$, CN, $CF_3$, $NHCOCH_3$, $OCH_3$, $SCH_3$, $NH_2$, $NHCH_3$, $OCOCH_3$, $OCOC_2H_5$, $OC_2H_5$, $OC_3H_7$, $CH_3$, $C_2H_5$, and $C_3H_7$;

$Y_2$ and $Y_3$ are the same or different and each is $NHCOR_4$, H, OH, $NHCOCH_3$, $NHCOC_2H_5$, Cl, F, Br, or I, or taken together is =O;

$Y_4$ is selected from the group consisting of $R_4$, $CH_2$, —$(CH_2)_n$—, O, S, and NH;

$L_3$ is an alkylene;

$R_{11}$ and $R_{12}$ are independently selected from the group consisting of H and substituted and unsubstituted alkyl; and HA is selected from the group consisting of nothing, hydrochloride, hydrobromide, hydroiodide, nitric acid, sulfic acid, bisulfic acid, phosphoric acid, phosphorous acid, phosphonic acid, isonicotinic acid, acetic acid, lactic acid, salicylic acid, citric acid, tartaric acid, pantothenic acid, bitartaric acid, ascorbic acid, succinic acid, maleic acid, gentisinic acid, fumaric acid, gluconic acid, glucaronic acid, saccharic acid, formic acid, benzoic acid, glutamic acid, methanesulfonic acid, ethanesulfonic acid, benzensulfonic acid, p-toluenesulfonic acid and pamoic acid.

9. A high penetration compound, or a pharmaceutically acceptable salt thereof, selected from the group consisting of:
(4-[bis(2-chloroethyl)amino]-N-acetyl-L-phenylalanine N,N-diethylaminoethyl ester);
(N,N-diethylaminoethyl 4-[bis(2-chloroethyl)amino]benzenebutyrate);
(diethylaminoethyl 4-[bis(2-methylsulfonylethyl)amino] benzenebutyrate); and
(N,N-bis(2-chloroethyl)aminophosphamide N,N-diethylaminoethyl ester hydrobromide).

10. A pharmaceutical composition comprising a high penetration compound of claim 9, or a pharmaceutically acceptable salt thereof, and a pharmaceutically acceptable carrier.

* * * * *